(12) United States Patent
Levi et al.

(10) Patent No.: US 6,884,809 B2
(45) Date of Patent: Apr. 26, 2005

(54) METHOD AND COMPOSITIONS FOR REDUCING CARDIAC DYSFUNCTIONS WITH A SELECTIVE HISTAMINE $H_3$ RECEPTOR AGONIST

(75) Inventors: Roberto Levi, New York, NY (US); Randi B. Silver, New York, NY (US)

(73) Assignee: Cornell Research Foundation, Inc., Ithaca, NY (US)

(*) Notice: Subject to any disclaimer, the term of this patent is extended or adjusted under 35 U.S.C. 154(b) by 308 days.

(21) Appl. No.: 10/076,204

(22) Filed: Feb. 13, 2002

(65) Prior Publication Data

US 2002/0151576 A1 Oct. 17, 2002

Related U.S. Application Data

(60) Provisional application No. 60/268,393, filed on Feb. 13, 2001, and provisional application No. 60/381,057, filed on Nov. 19, 2001.

(51) Int. Cl.[7] ..................... A61K 31/445; A61K 31/415

(52) U.S. Cl. ..................... 514/326; 514/397; 514/399

(58) Field of Search ..................... 514/399, 326, 514/397

(56) References Cited

U.S. PATENT DOCUMENTS

| | | |
|---|---|---|
| 5,821,259 A | 10/1998 | Theoharides |
| 5,908,853 A | 6/1999 | Nahoum |
| 6,136,559 A | 10/2000 | Lovenberg et al. |
| 6,159,994 A | 12/2000 | McDonald et al. |

FOREIGN PATENT DOCUMENTS

WO    WO/00/20011    4/2000

OTHER PUBLICATIONS

Avery's Drug Treatment, 3rd edition (1987), pp. 611 and 614–621.*
Database CAPLUS on STN, (Columbus, OH, USA), No. 122:78176, Unmasking of activated H3–receptors in myocardial ischemia: their role as regulators of exocytotic norepinepherine release, *J. Pharmacology. Exp. Ther.*, Imamura et al., 1994, 27(3):1259–1266 (abstract only).
Database CAPLUS on STN, (Columbus, OH, USA), No. 117:226854, Inhibition of sympathetic hypertensive response in the guinea pig by prejunctional histamine H3–receptors, *Br. J. Pharmacol.*, Hey et al., 1992, 107(2):347–351 (abstract only).
Database CAPLUS on STN, (Columbus, OH, USA), No. 123:48330, Functional identification of histamine H3–receptors in the human heart. Circ. Res., Imamura et al., 1995, 77(1):206–210 (abstract only).

Hatta et al., "Activation of Histamine $H_3$ Receptors Inhibits Carrier–Mediated Norepinephrine Release in a Human Model of Protracted Myocardial Ischemia", *The Journal of Pharmacology and Experimental Therapeutics* 1997, 283(2):494–500.
Mackins et al., "Therapeutic potential of $H_3$–receptor agonists in myocardial infarction", *Exp. Opin. Invest. Drugs* 2000, 9(11):1–6.
Karmazyn et al., "The Myocardial $Na^+$–$H^+$ Exchange Structure, Regulation, and Its Role in Heart Disease", *Circulation Research* 1999, 85:777–786.
Kockskämper et al., "Activated of the cAMP–protein kinase A pathway facilitates $Na^+$ translocation by the $Na^+$–$K^+$ pump in guinea–pig ventricular myocytes", *Journal of Physiology* 2000, 523.3:561–574.
Leurs et al., "Therapeutic potential of histamine $H_3$ receptor agonists and antagonists", *TiPS* 1998, 19:177–183.
Mazenot et al., "In vivo demonstration of $H_3$–histaminergic inhibition of cardiac sympathetic stimulation by R–α–methyl–histamine and it prodrug BP 2.94 in the dog", *British Journal of Pharmacology* 1999, 126:264–268.
Rupprecht et al., "Cardioprotective Effects of the $Na^+$/$H^+$ Exchange Inhibitor Cariporide in Patients with Acute Anterior Myocardial Infarction Undergoing Direct PTCA", *Circulation* 2000, 101:2902–2908.
Silver et al., "Coupling of histamine $H_3$ receptors to neuronal $Na^+$/$H^+$ exchange: A novel protective mechanism in myocardial ischemia", *PNAS* 2001, 98(5):2855–2859.
Theroux, "Myocardial Cell Protection A Challenging Time for Action and a Challenging Time of Clinical Research", *Circulation* 2000, 101:2874–2876.
Wellman et al., "ATP–sensitive $K^+$ channel activation by calcitonin gene–related peptide and protein kinase A in pig coronary arterial smooth muscle", *Journal of Physiology* 1998, 507.1:117–129.
B Malinowska, et al., "Histamine $H_3$ Receptors—General Characterization and Their Function in the Cardiovascular System", *Journal of Physiology and Pharmacology*, 1998. 49(2):191–211.
H. van der Goot, et al., "Isothiourea Analogues of Histamine as Potent Agonists or Antagonists of the Histamine $H_3$–Receptor" *Eur. J. Med. Chem.* 1992. 27: 511–517.

(Continued)

Primary Examiner—Raymond J Henley, III
(74) Attorney, Agent, or Firm—Hoffmann & Baron, LLP; Irving N. Feit

(57) ABSTRACT

The invention provides a method for reducing cardiac dysfunctions in a human. The method comprises administration to the human of an effective amount of a selective histamine $H_3$ Receptor agonist. In one embodiment, the method comprises limiting the accumulation of intracellular sodium ($Na_i$) by inhibiting the $Na^+$/$H^+$ exchanger activity in the human having a cardiac dysfunction, or a predisposition to a cardiac dysfunction. In another embodiment the method comprises inhibiting the N-type $Ca^{2+}$ channel to modulate the concentration of intracellular calcium. The invention also provides a pharmaceutical composition that includes a selective histamine $H_3$ Receptor agonist with a pharmaceutical carrier.

30 Claims, 15 Drawing Sheets

OTHER PUBLICATIONS

Iwan J.P. De Esch, et al., "Characterization of the Binding Site of the Histamine $H_3$ Receptor. 1. Various Approaches to the Synthesis of 2–(1H–Imidazol–4–yl) cyclopropylamine and Histaminergic Activity of (1R,2R)– and (1S, 2S)–2–(1H–Imidazol–4–yl)–cyclopropylamine", *Journal of Medicinal Chemistry*, 1999. 42(7): 1115–1122.

Christina J. Mackins, et al., "Therapeutic Potential of $H_3$–receptor Agonists in Myocardial Infarction", *Exp. Opin. Invest Drugs* 2000. 9(11): 2537–2542.

Catherine Mazenot, et al., "Histamine $H_3$–receptor Stimulation is Unable to Modulate Noradrenaline Release by the Isolated Rat Heart During Ischaemia–Reperfusion", *Fundam. Clin. Pharmacol.* 1999. 13(4): 455–60.

Catherine Mazenot, et al., "In vivo Demonstration of $H_3$–histaminergic Inhibition of Cardiac Sympathetic Stimulation by R–α–methyl–histamine and its Prodrug BP 2.94 in the Dog", *British Journal of Pharmacology* 1999. 126: 264–268.

Pierre Theroux, M.D., "Myocardial Cell Protection. A Challenging Time for Action and Challenging Time of Clinical Research", *Circulation* 2000.

Hans–Jurgen Rupprecht, M.D., et al., "Cardioprotective Effects of the $Na^+/H^+$ Exchange Inhibitor Cariporide in Patients with Acute Anterior Myocardial Infarction Undergoing Direct PTCA", *Circulation* 2000. 101:2902–2908.

Morris Karmazyn, et al., "The Myocardial $Na^+–H^+$ Exchange. Structure, Regulation and Its Role in Heart Disease", *Circulation Research* 1999. 85:777–786.

Eiichiro Hatta, et al., "Activation of Histamine $H_3$ Receptors Inhibits Carrier–Mediated Norepinephrine Release in a Human Model of Protracted Myocardial Ischemia", *Journal of Pharmacology and Experimental Therapeutics* 1997. 283:494–500.

Randi B. Silver, et al., "Coupling of Histamine $H_3$ Receptors to Neuronal $Na^+/H^+$ Exchange: A Protective Mechanism in Myocardial Ischemia", *PNAS Early Edition* 2001. 1–5.

Rob Leurs, et al., "Therapeutic Potential of Histamine $H_3$ Receptor Agonists and Antagonists", *Trends in Pharmacological Sciences* 1998. 19:177–183.

P.K. Rangachari, "The Fate of Released Histamine: Reception, Response and Termination", *Yale Journal of Biology and Medicine* 1998. 71:173–182.

Randi B. Silver, et al., "Coupling of Histamine $H_3$ receptors to Neuronal $Na^+/H^+$ Exchange: A Novel Protective Mechanism in Myocardial Ischemia", *PNAS* 2001. 98(5):2855–2859.

Michiaki Imamura, et al., "Activation of Histamine $H_3$–Receptors Inhibits Carrier–Mediated Norepinephrine Release During Protracted Myocardial Ischemia", *Circ. Res.* 1996. 78:475–481.

Roberto Levi, et al., "Histamine $H_3$–Receptors: A New Frontier in Myocardial Ischemia", *The Journal of Pharmacology and Experimental Therapeutics* 2000. 292:825–830.

H.D. Holtje, et al., "Molecular Modelling Studies on Histamine $H_2$– and $H_3$– Receptor Agonists", www.pharm.uni-duesseldorf.de/forschung/mitabeiter/sippl/Maastricht.pdf. 1–12 No date available.

Patrizio Blandina, "The Role of Interactions Between Histaminergic and Cholinergic Systems in Learning and Memory", www.mcmaster.ca/inabis98/huston/blandina0227/two.html (No date available).

Rob Leurs, et al., "Histamine Receptors", *Tocris cookson*. www.biotrend.com/pdf/histamine.pdf. 1–6 (no date available).

Akagi, et al., "Role of histamine $H_3$ receptor on hypoxia–reoxygenation–induced cardiac dysfunction in guinea pigs", PubMed No. 8750792, *Methods Find Exp. Clin. Pharmacol.*, 1995, vol. 17 Suppl C:30–35. (abstract only).

Imamura, Michiaki, et al., "Histamine $H_3$–Receptor–Mediated Inhibition of Calcitonin Gene–Related Peptide Release From Cardiac C Fibers", *Circulation Research* 1996, 78(5):863–869.

Luo, Xiao–Xing, et al., "Histamine $H_3$–receptors inhibit sympathetic neurotransmission in guinea pig myocardium", *European Journal of Pharmacology* 1991, 204:311–314.

* cited by examiner

METHOD AND COMPOSITIONS FOR REDUCING CARDIAC DYSFUNCTIONS WITH A SELECTIVE HISTAMINE H₃ RECEPTOR AGONIST

This application claims the benefit of provisional application, U.S. Ser. No. 60/268,393 which was filed Feb. 13, 2001 and provisional application, U.S. Ser. No. 60/381, 057 filed Nov. 19, 2001. The specifications of the above-identified provisional applications are hereby incorporated by reference in their entirety.

The invention described herein was made with funds from the National Institutes of Health under grant numbers DK45828, HL 34215 and HL 46403. Therefore, the government has certain rights in the invention.

BACKGROUND OF THE INVENTION

Myocardial ischemia and infarction are associated with excessive norepinephrine (NE) release from sympathetic nerve endings (See reference 1). Cardiac dysfunctions, such as arrhythmias ensue, resulting in high morbidity and mortality. (References 2, 3). In these pathological conditions, NE is released principally by a reversal of the normal NE re-uptake pathway (NE transporter) in cardiac sympathetic nerves. This is known as "carrier mediated" release of NE in contrast to the normal exocytotic release of NE. Several lines of evidence suggest that changes in intracellular sodium ($Na_i$) influence this pathological NE release.

The anoxia resulting from myocardial ischemia perturbs the metabolism of the neuron and is characterized by intracellular acidosis, depletion of ATP stores, and accumulation of free NE in the axoplasm. A consequence of this pathological state is compromised function of the $Na^+$ pump ($Na^+/K^+$ ATPase), which leads to accumulation of $Na_i$. In addition, the intracellular acidosis activates the $Na^+/H^+$ exchanger (NHE) whose function is dependent on intracellular pH. NHE extrudes intracellular $H^+$ in exchange for extracellular $Na^+$. NHE activation exacerbates the accumulation of $Na_i$ and thereby favors the release of free NE via the NE transporter ("carrier mediated" NE release).

Histamine H₃ receptors (H₃R, reference 7) were recently discovered to be present in cardiac sympathetic nerve endings. (References 8–10). To date, however, there has been no direct link between stimulation of histamine H₃ receptors and inhibition of $Na^+/H^+$ exchanger activity or any other mechanism capable of regulating $Na^+$ ion transfer in sympathetic nerve endings (SNEs). These mechanisms include the action of $Na^+/K^+$ ATPase, the voltage-dependent $Na^+$ channel, the $Na^+/Ca^{++}$ exchanger, the $Na^+/K^+$ exchanger and any plasma membrane protein that can mediate a change in the intracellular $Na^+$ concentration in SNEs.

Furthermore, in addition to the mechanisms that may be involved in increasing $Na_i$, any mechanism that may be involved in modulating $H^+_i$, such as one involving $H^+_i$/ATPase, or a mechanism involved in modulating $Ca_i$, e.g. modulation of the L-$Ca^{2+}$ channel, may play a major role in producing conditions that favor the pathological carrier mediated release of NE under ischemic conditions.

In the absence of direct evidence implicating a particular mechanism, there is no reasonable likelihood that stimulation of histamine H₃ receptors will decrease norepinephrine release associated with a pathological condition, such as myocardial ischemia in humans. Similarly, absent such direct evidence, there is no reasonable likelihood that such decrease in norepinephrine release will successfully treat cardiac dysfunctions resulting from excessive norepinephrine (NE) release under these conditions.

Moreover, in the rat, an animal model for the intact human, it has been shown that an H₃ receptor agonist failed to modulate release of NE associated with a pathological condition, such as ischemia-reperfusion. See reference 23, which is entitled "Histamine H₃-receptor stimulation is unable to modulate noradrenaline (NE) release by the isolated rat heart during ischemia-reperfusion."

There is an urgent need for methods and pharmaceutical compositions that are capable of reducing cardiac dysfunctions, such as those cardiac dysfunctions that are associated with ischemia that may result in cardiac infarctions in a human.

SUMMARY OF THE INVENTION

These and other objectives have been achieved by providing a method for reducing cardiac dysfunctions in a human in need thereof. The method comprises administering to the human an effective amount of a selective histamine H₃ receptor agonist. In one embodiment, the method comprises inhibiting the $Na^+/H^+$ exchanger activity in a human having a cardiac dysfunction. In another embodiment the method comprises decreasing $Ca_i$ concentration by inhibiting $Ca^{2+}$ influx through N-type $Ca^{2+}$ channels. In yet another embodiment, the invention provides a pharmaceutical composition comprising a selective histamine H₃ receptor agonist in a pharmaceutical carrier. Optimally, the histamine H₃ receptor agonist is specific for the histamine H₃ receptor over other histamine receptor subtypes, including the histamine H₁ receptor and the histamine H₂ receptor.

DETAILED DESCRIPTION OF THE INVENTION

Figure 1A:
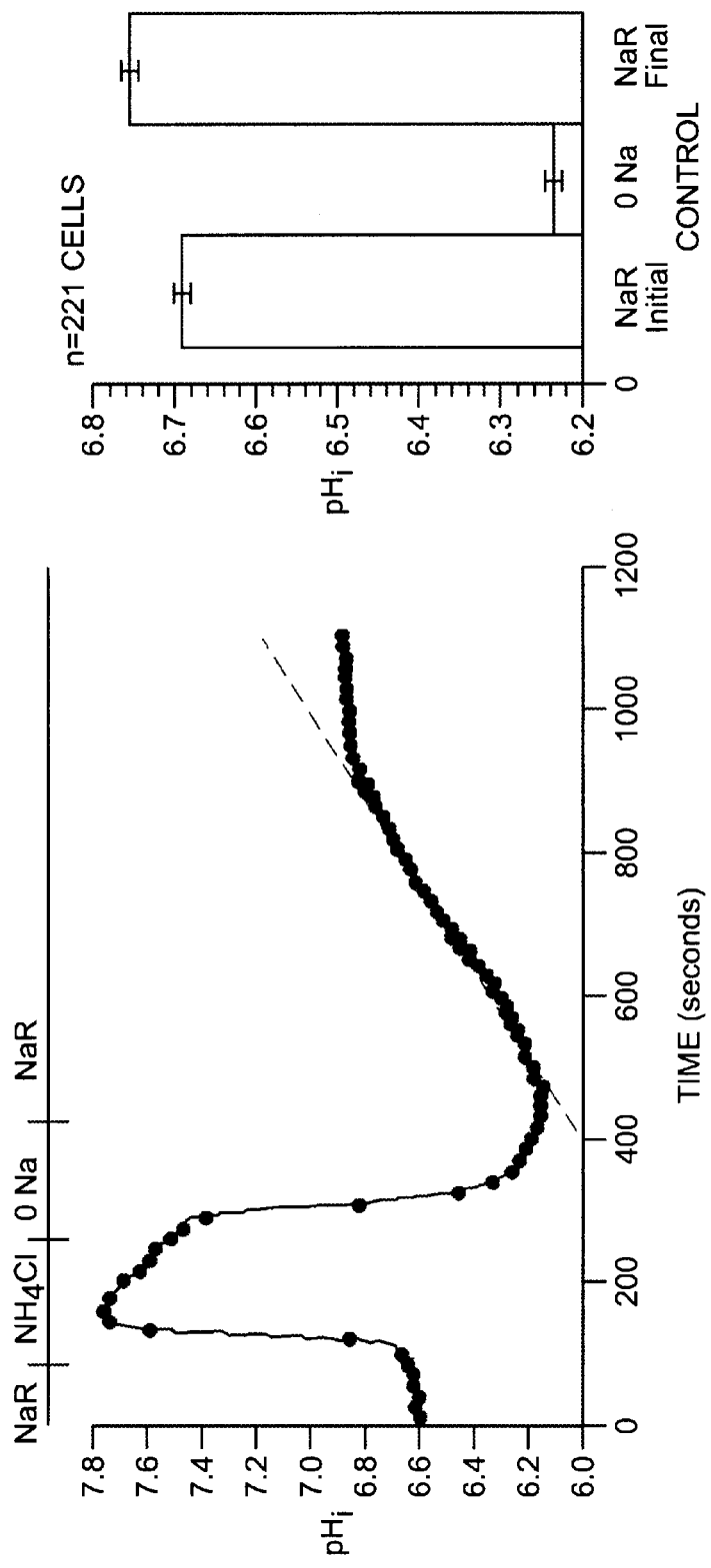
FIG. 1. Representative experimental traces from individual human neuroblastoma SKNMC-H₃ cells showing the $Na^+$-dependent $pH_i$ recovery after acute exposure to an $NH_4Cl$ acid pulse. The Y-axis represents the $pH_i$ as determined from the intracellular calibration of the dye in this cell.
Panel A. Control Cells.
Panel B. Effect of Imetit.
The bar graphs show the mean steady state $pH_i$ achieved before and after activation of NHE in the absence and presence of imetit.

The present inventors have, at last, been able directly to demonstrate that stimulation of histamine $H_3$ receptors decreases the activity of NHE, the $Na^+/H^+$ exchanger. This discovery by the inventors leads to what has been sorely lacking from the prior art, namely a method having more than a reasonable expectation that a selective histamine $H_3$ receptor agonist will successfully reduce cardiac dysfunctions in a human.

The cardiac dysfunction treated by the method is any cardiac dysfunction that is caused by excessive accumulation of $Na_i$ in the cardiac neurons. The dysfunction may, for example, be caused by myocardial ischemia or myocardial infarction. Some examples of cardiac dysfunctions include arrhythmia, fibrillation, platelet activation and aggregation, thrombus formation, coronary spasm, cardiac failure or in extreme cases, sudden cardiac death.

The selective histamine $H_3$ receptor agonist is any biological or organic molecule that stimulates histamine $H_3$ receptors to inhibit the $Na^+/H^+$ exchanger in the human. The agonist is selective if it causes activation of the histamine $H_3$ receptor to an extent significantly greater than any other histamine receptor, such as, for example, the histamine $H_1$ receptor or the histamine $H_2$ receptor.

Inhibition, for the purposes of this application is defined as any reduction in activity caused by an inhibitor. The inhibition caused by an inhibitor may be complete inhibition of the activity that is inhibited, resulting in complete loss of the activity inhibited. Alternatively, the inhibition may be partial inhibition of the inhibited activity, resulting in a reduction in the activity that is inhibited.

The $H_3$ receptor agonists herein described are small molecules or biological molecules. Biological molecules include all lipids and polymers of monosaccharides, amino acids and nucleotides having a molecular weight greater than 450. Thus, biological molecules include, for example, oligosaccharides and polysaccharides; oligopeptides, polypeptides, peptides, and proteins; and oligonucleotides and polynucleotides.

Biological molecules further include derivatives of any of the molecules described above. For example, derivatives of biological molecules include lipid and glycosylation derivatives of oligopeptides, polypeptides, peptides and proteins. Derivatives of biological molecules further include lipid and glycosylated derivatives of oligosaccharides and polysaccharides, e.g. lipopolysaccharides.

Any molecule that is not a biological molecule is considered in this specification to be a small molecule. Accordingly, small molecules include organic compounds, organometallic compounds, salts of organic and organometallic compounds, saccharides amino acids, and nucleotides. Small molecules further include molecules that would otherwise be considered biological molecules, except their molecular weight is not greater than 450. Thus, small molecules may be lipids, oligosaccharides, oligopeptides, and oligonucleotides, and their derivatives, having a molecular weight of 450 or less.

It is emphasized that small molecules can have any molecular weight. They are merely called small molecules because they typically have molecular weights less than 450. Small molecules include compounds that are found in nature as well as synthetic compounds.

A variety of histamine $H_3$ receptor agonists are well known. Some examples of selective histamine $H_3$ receptor agonists include the following: R-α-methylhistamine, S-α-chloromethylhistamine, R-α-S-β-dimethylhistamine, cyclopropylhistamine, 4-(1H-4-imidazolylmethylene)-1-methylpiperidine, Imetit, Immepip, Immepyr, VUF 4864, VUF 5296, VUF 5297, VUF 8325, SKF 91606, and Sch 50971.

The structure of histamine, the cognate ligand of the $H_3$ receptor and the structures of these $H_3$ receptor agonists are shown below:

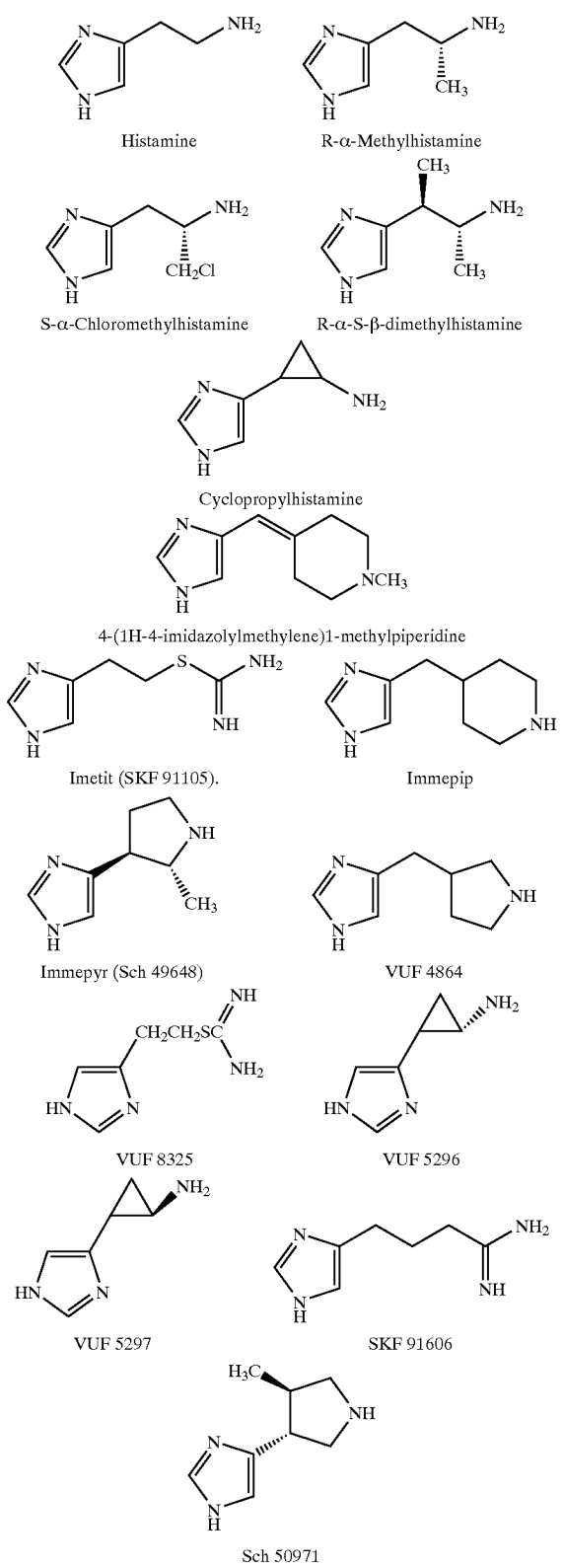

The $H_3R$ agonist, Imetit (SKF 91105) is available from Calbiochem (San Diego, Calif.) as the dihydrobromide salt. R-α-Methylhistamine is available from Sigma-Aldrich (St.Louis, Mo.). The $H_3R$ agonist, immepip is available from Tocris Cookson (Ellisville, Mo.). The structure and activity of SKF 91606 is disclosed in Howson et al. (1992) *Bioorg Med. Chem. Lett.* 2:77–78 and in van der Groot et al. (1992) *Eur. J. Med. Chem. Chem.* 27:511–517. The synthesis and activity of VUF 8325 is disclosed in van der Groot et al. (1992) ibid. The scheme for synthesis and the activities of stereoisomers VUF 5296 and VUF 5297 are disclosed in De Esch et al. (1999) *J. Med. Chem.*42(7):1115–1122. The synthetic methods disclosed in the above-cited Howson et al., van der Groot et al. and De Esch et al. references are hereby incorporated by reference in their entirety.

These $H_3$ receptor agonists are specifically antagonized by $H_3$ receptor antagonists such as Thioperamide (available from Sigma-Aldrich, St. Louis, Mo.) and Clobenpropit (available from Tocris-Cookson, Ellisville, Mo.). The structures of these $H_3$ receptor antagonists are as follows:

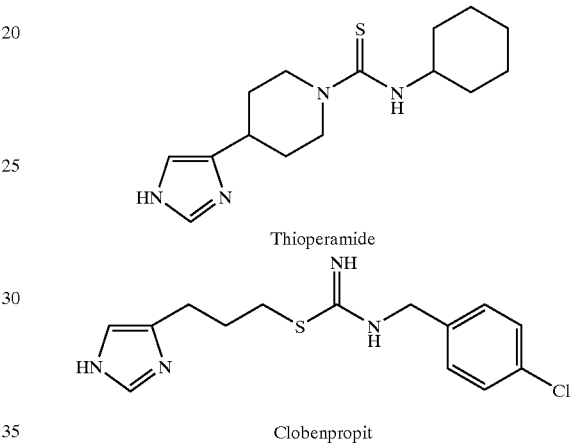

The selective histamine $H_3$ receptor agonist may be administered as a protective measure to a human patient predisposed to a cardiac dysfunction, or as a therapeutic measure to a human patient who suffers from a cardiac dysfunction. The selective histamine $H_3$ receptor agonist may be administered, for example, to a human patient before or after the onset of myocardial ischemia and/or myocardial infarction.

The selective histamine $H_3$ receptor agonist acts on the cells of the nervous system that express the $H_3$ receptor, including cells of the central nervous system (CNS), cells of the peripheral nervous system (PNS), or both. Alternatively, in another embodiment the selective histamine $H_3$ receptor agonist does not act on the central nervous system. For example, the selective histamine $H_3$ receptor agonist may not cross the blood brain barrier.

In yet another embodiment, the histamine $H_3$ receptor is on a cardiac sympathetic nerve ending. In one example of this embodiment the histamine $H_3$ receptor agonist reduces norepinephrine release from the cardiac sympathetic nerve ending.

In one aspect of the invention, the histamine $H_3$ receptor agonist decreases the accumulation of intracellular sodium ($Na_i$). In another aspect, the histamine $H_3$ receptor agonist decreases the accumulation of intracellular calcium ($Ca_i$).

In another embodiment, the histamine $H_3$ receptor agonist decreases the $Na^+/H^+$ exchanger (NHE) activity in a human having a cardiac dysfunction. The agonist may, for example, diminish the $Na^+/H^+$ exchange at sympathetic nerve endings in the human.

In yet another aspect, the histamine $H_3$ receptor agonist decreases the flux through N-type $Ca^{2+}$ channels in a human having a cardiac dysfunction. The agonist may, for example, diminish the $Ca_i$ in the sympathetic nerve endings in the human.

In yet another embodiment, the histamine $H_3$ receptor agonist is delivered in combination with other agents in the treatment of cardiac dysfunction. Some examples of such other agents include β-blockers, $Ca^{2+}$-channel blockers, anti-arrhythmics, angiotensin converting enzyme (ACE) inhibitors and angiotensin receptor antagonists (such as, for instance, Losartan).

The selective histamine $H_3$ receptor agonist may be administered in an effective amount. An effective amount is any amount of the selective histamine $H_3$ receptor agonist that reduces a cardiac dysfunction in a human by, for example, inhibiting the $Na^+/H^+$ exchanger or inhibiting influx of $Ca^{2+}$ into a cardiac cell by inhibiting influx of $Ca^{2+}$ via the N-type $Ca^{2+}$ channel.

Effective amounts are routinely determined by physicians conducting clinical trials. Some examples of effective amounts include a minimum of about 0.01 mg, preferably about 0.05 mg, and more preferably about 0.1 mg; and a maximum of about 500 mg, preferably about 100 mg, and more preferably about 50 mg. Most preferably, the effective amount of the selective histamine $H_3$ receptor agonist is between about 0.5 mg and about 5 mg.

The invention includes pharmaceutical compositions comprising a selective histamine $H_3$ receptor agonist, such as those described above, in a pharmaceutical carrier. Pharmaceutical carriers include any kind of formulation suitable for delivering drugs to humans. The composition may be administered, for example, topically, enterally or parenterally. Enteral administration may be for instance, orally. Parenteral administration may be for instance intramuscularly, subcutaneously, intraperitoneally or intravenously.

Pharmaceutical carriers that may be employed with the histamine $H_3$ receptor agonist compositions of the present invention include neutral buffers such as Tris.HCl and phosphate buffers at about pH 7 with, or without added NaCl. Optionally the pharmaceutical carrier may also contain an inert material as a vehicle or bulking agent and may also contain a preservative, such as for example, an antioxidant. Many pharmaceutically acceptable substances are well known to those of skill in the art, including for example, pharmaceutical carriers, solvents, salts, excipients, physiological substances and bulking agents. Some examples of pharmaceutical carriers include liquid solutions such as sterile water, sterile saline solutions and suspensions, syrups and solid ingredients for formulating pills, powders, etc.

The present invention particularly concerns pharmaceutical compositions comprising an histamine $H_3$ receptor agonist in a pharmaceutically acceptable carrier. The pharmaceutical compositions comprising an histamine $H_3$ receptor agonist according to the present invention are admixed with a pharmaceutically acceptable substance to form pharmaceutical compositions suitable for clinical administration.

The pharmaceutical compositions of the present invention may be produced under GLP (Good Laboratory Practice) or GMP (Good Manufacturing Practice) conditions and are preferably of clinical grade. Particularly favored pharmaceutical compositions of the present invention are produced under GMP and are of clinical grade as required by the United States Food and Drug Administration (FDA).

EXAMPLES

SKNMC-$H_3$ Cell preparation and BCECF-loading.
SKNMC-$H_3$ cells (See reference 12) were grown to confluence (2 days after plating) on 22-mm square standard glass coverslips (No. 1) and maintained in α-modified Eagles's medium supplemented with 10% fetal bovine serum, 2 mM L-glutamine, 450 ug/ml geneticin, 50 units/ml penicillin and 50 ug/ml streptomycin at 37° C., 5% $CO_2$. Cells were loaded with the membrane-permeant form of the $pH_i$ indicator 2',7'-bis(carboxyethyl)-5(6)-carboxyfluorescein (BCECF) ester (5 μM) for 20 min at room temperature. After loading with the dye, cells were rinsed with Hepes-buffered $Na^+$ Ringer's solution (140 mM NaCl, 5 mM KCl, 10 mM Hepes, 2 mM $CaCl_2$, 1 mM $MgCl_2$, pH 7.4). The coverslip with the BCECF-loaded cells was attached to the bottom of a flow-through superfusion chamber and mounted on the stage of an inverted epifluorescence microscope (Nikon Diaphot). The cells in the chamber were superfused and maintained at 37° C. as previously described (references 15, 16). Cells were visualized under transmitted light with a Nikon CF Fluor oil immersion objective (x40/1.3 na) before starting the fluorescence measurements. Calibration of the emitted fluorescence signal from each cell in the field was performed at the end of each experiment according to the nigericin/high $K^+$ method (reference 17). Cells in the experimental field of view were analyzed singularly and independently from their neighbors.

Preparation of Cardiac Synaptosomes.

Male Hartley guinea pigs (Charles River, Wilmington, Mass.) weighing 250–300 grams were sacrificed by cervical dislocation under light anesthesia with $CO_2$ vapor. The ribcage was rapidly opened and the heart dissected away. A cannula was inserted in the aorta and the heart was perfused for 5 min at constant pressure (40 cm $H_2O$) in a Langendorff apparatus (reference 25) with Ringer's solution (containing NaCl 154 mM; KCl 5.61 mM; $CaCl_2$ 2.16 mM; $NaHCO_3$ 5.95 mM; and glucose 5.55 mM) equilibrated with 100% $O_2$ at 37° C. This procedure ensured that no blood traces remained in the coronary circulation. Hearts were then freed from fat and connective tissue and minced in ice-cold 0.32 M sucrose containing 1 mM EGTA, pH 7.4. Synaptosomes were isolated as previously described (reference 10), with the following modifications. Minced tissue was digested with 40–75 mg collagenase (type II, Worthington Biochemicals; Freehold, N.J.) per 10 ml HEPES-buffered saline solution (HBS: containing 50 mM HEPES, pH 7.4, 144 mM NaCl, 5 mM KCl, 1.2 mM $CaCl_2$, 1.2 mM $MgCl_2$, 10 mM glucose and 1 mM pargyline (pargyline hydrochloride, Sigma-Aldrich Co; St. Louis, Mo.), to prevent enzymatic destruction of synaptosomal NE) per gram wet heart weight for 1 hour at 37° C. After low speed centrifugation (10 min at 120 g at 4° C.), the resulting pellet was suspended in 10 volumes of 0.32 M sucrose and homogenized with a Teflon/glass homogenizer. The homogenate was spun at 650 g for 10 min at 4° C. and the pellet rehomogenized and respun. The pellet, which contained cellular debris, was discarded and the supernatants from the last two spins were combined and equally subdivided into 10–12 tubes. Each tube was centrifuged for 20 min at 20,000 g at 4° C. Each pellet, which contained cardiac synaptosomes, was resuspended in HBS to a final volume of 500 μl and incubated with KCl (3–30 mM) in the presence or absence of pharmacological agents in a water bath at 37° C. Each suspension functioned as an independent sample and was used only once. In every experiment, one sample was untreated (control, basal release) and the others were treated with high $K^+$ alone, high $K^+$ and drugs, or with drugs alone. When high $K^+$ was used, osmolarity was maintained constant by adjusting the NaCl concentration. Treated samples were incubated with a given agent for 20 min and then with high $K^+$ for 5 min. When antagonists were used, samples were incubated with the antagonist for 10 min prior to incubation with the agonist. Controls were incubated for an equivalent length of time without drugs. At the end of the incubation period each sample was centrifuged again for 20 min (20,000 g at 4° C.). The supernatant was assayed for NE content by high pressure liquid chromatography with electrochemical detection (reference 5). The pellet was assayed for protein content, by a modified Lowry procedure (12).

SH-SY5Y Parent Cells:

The human neuroblastoma SH-SY5Y cell line, Eagles' minimal essential medium (MEM), Ham's F-12 nutrient mixture and fetal bovine serum were obtained from ATCC (Manassas, Va.). Trypsin, phosphate-buffered saline, Geneticin, glutamine, penicillin and streptomycin were purchased from Gibco (Rockville, Md.). Desipramine hydrochloride, EGTA, imetit dihydrobromide, thioperamide maleate, Triton-X-100 and ω-conotoxin GVIA were obtained from Sigma-Aldrich Co. (St. Louis, Mo.). [$^3$H] norepinephrine (28.0 Ci/mmol) ([$^3$H]NE) was purchased from Amersham Life Science (Arlington Heights, Ill.). Ionomycin was obtained from Calbiochem (San Diego, Calif.). Fura-2 AM was obtained from Molecular Probes (Eugene, Oreg.).

Tissue Culture:

SH-SY5Y cells were cultured using a 1:1 ratio of Eagles' MEM and Ham's F-12 nutrient mixture, supplemented with 10% fetal bovine serum, 2 mM glutamine, 50U/ml penicillin and 50 μg/ml streptomycin (complete medium), maintained at 37° C. in 5% $CO_2$. Cells were plated four days before the [$^3$H]NE release experiments onto 6-well plates; for $Ca_i$ measurements, cells were grown on 22-mm$^2$ standard glass cover slips (No. 1).

[$^3$H]NE Release Assay:

The [$^3$H]NE release method was adapted from that described by Murphy et al. (reference 29). Culture medium was removed and cells were washed once with HEPES buffer (2.6 mM $CaCl_2$, 25 mM HEPES, 1.2 mM $MgSO_4$, 5.6 mM glucose, 1.2 mM $KH_2PO_4$, 125 mM NaCl, 4.8 mM KCl and 0.2 mM pargyline, pH 7.4), then incubated in 1 ml per well of HEPES buffer containing 50 nM [$^3$H]NE for 60 min at 37° C. This was followed by three washes per well with 1 ml HEPES buffer (containing 1 μM desipramine). One ml of release buffer (HEPES buffer with 100 mM K$^+$, adjusted to maintain osmolarity) was then added to each well for 3 min at room temperature. A 300 μl aliquot of the supernatant was taken from each well for counting and the remaining solution was discarded. One ml (0.3%) Triton-X-100 was added to the cells for 30 min, and 300 μl lysate was taken for counting. Samples taken for counting were each added to 4 ml of Bio-Safe II scintillation cocktail and counted on a Beckman LS6000 scintillation counter. For drug experiments, after the three washes cells were incubated in 1 ml of HEPES buffer containing the given drug for 10 min at 37° C., followed by release as described above. [H]NE release was expressed as a percentage of the total [$^3$H]NE content.

Transfection of SH-SY5Y Cells with the Human $H_3$ Receptor.

Cells were grown to 70–80% confluence and removed from the plate with trypsin and pelleted in a clinical centrifuge. The pellet was then resuspended in 400 μL complete medium and transferred to an electroporation cuvette with a 0.4 cm gap between the electrodes (Bio-Rad #165–2088). One μg supercoiled $H_3R$ cDNA was added to the cells and mixed. The voltage for the electroporation was set at 0.25 kV, the capacitance was set at 960 μF. After electroporation the cells were diluted into 10 ml complete medium and were plated onto four 10-cm dishes at the following ratios; 1:20, 1:10, 1:5, 1:2. The cells were incubated for 24 hours before adding 100 μg/ml Geneticin. Colonies that survived selection were isolated and expanded for testing. Because these cells grow poorly in Geneticin, 4 days after isolation Geneticin was completely removed from the medium. The individual clones were then tested for binding to [$^3$H]Na-methyl-histamine as described in Lovenberg et al. (14).

$Ca_i$ Measurements.

Cells grown on cover slips were loaded with the membrane-permeant form of the $Ca_i$ indicator Fura-2 ester (5 μM) for 20 min at room temperature. After loading with the dye, the cells were rinsed with HBS Na Ringer's solution (140 mM NaCl, 5 mM KCl, 10 mM HEPES, 2.6 mM $CaCl_2$, 1.0 mM $MgCl_2$, pH 7.4). The coverslip was attached to the bottom of a flow-through superfusion chamber and mounted on the stage of an inverted epifluorescence microscope (Nikon Diaphot). The cells in the chamber were superfused and maintained at 37° C. as previously described (reference 15). Cells were first visualized under transmitted light with a Nikon CF Fluor (x40/1,3 NA oil immersion objective) before starting fluorescence measurements. Cells were depolarized with a high-K$^+$ solution (based on the Na Ringer's composition described above with 100 mM KCl replacing 100 mM NaCl). Calibration of the emitted Fura-2 signal from each cell in the field was carried out in the presence of the $Ca^{2+}$ ionophore, ionomycin (10 M) in the presence of HEPES buffer containing either 2.6 mM $Ca^{2+}$ or 10 mM EGTA titrated to pH 7.4. $Ca_i$ levels were calculated as described by Grynkiewicz et al. (16). Cells in the experimental field of view were analyzed singularly and independently from their neighbors.

Solutions and Reagents.

The experimental solutions were based on the Na$^+$ Ringer's composition described above with the following substitutions: for the $NH_4Cl$ solution, NaCl and KCl were replaced with 20 mM $NH_4Cl$ and 120 mM N-methyl-D-glucamine (NMDG/Cl); for the Na$^+$-free solution, NaCl and KCl were replaced with 145 mM NMDG/Cl. The Na$^+$-free solutions were titrated to pH 7.4 with NMDG powder. The composition of the high K$^+$-calibration solutions was similar to that of Na$^+$-Ringer, except that NaCl was replaced with KCl, and titrated with KOH to pH 6.5 and pH 7.8, respectively, as previously described (reference 18). All chemicals were obtained from Sigma Chemical Co. unless otherwise stated. Imetit (RBI, Natick, Mass.) was prepared in distilled water and then diluted 1:10,000 to yield a final concentration of 100 nM in the experimental superfusates. Thioperamide (300 nM), an $H_3R$ antagonist (reference 19), and 5-(N-ethyl-N-isopropyl)amiloride (EIPA; 10 μM), an inhibitor of NHE (reference 20), were both diluted in dimethyl sulfoxide. Nigericin, a K$^+$/H$^+$ exchanger, was added to the K$^+$ calibration solutions from a 20 mM stock made up in ethanol to yield a final concentration of 10 μM. Individual vials (50 ug) of the acetoxymethyl derivative of BCECF (Molecular Probes, Eugene, Oreg.) were stored dry at 0° C. and reconstituted in dimethyl sulfoxide, at a concentration of 10 μM, for each experiment. Ionomycin was prepared in dimethyl sulfoxide to give a final concentration of 10 μM. Individual vials (50 μg) of the acetoxymethyl derivative of Fura-2 were stored dry at 0° C. and reconstituted in dimethyl sulfoxide, at a concentration of 5 mM, for each experiment. At the concentrations used, dimethyl sulfoxide and ethanol had no effect on any preparation in these studies.

Equipment.

The basic components of the experimental apparatus have been described previously (references 21, 22). The imaging work station was controlled with the Metafluor software package (Universal Imaging, Westchester, Pa.). In experiments where fluorescence of BCECF was measured, the image pairs were obtained every 15 sec for the duration of the experiment at 490 nm and 440 nm excitation with emission at 520 nm. In experiments using Fura-2, quantitative image pairs at 340 nm and 380 nm excitation with emission at 510 nm, were obtained every 15 sec as before or every 0.1 second immediately preceding and during depolarization. The fluorescence excitation was shuttered off except during the brief periods required to record an image. To check for interference from intrinsic autofluorescence and background, images were obtained on cells using the same exposure time and filter combination used for the experiments, and found to be a minor component of the fluorescence signal.

To test the hypothesis that $H_3R$ activation diminishes NHE activity, individual SKNMC-$H_3$ cells loaded with the $pH_i$ indicator, BCECF were assayed for NHE activity. The response of these cells to an acute acid load was assessed in the absence or presence of the selective $H_3R$ agonist, imetit (reference 13), either alone or in combination with the selective $H_3R$ antagonist, thioperamide (reference 19). FIG. 1, shows the $pH_i$ response to a pulse of $NH_4Cl$ in a control cell (panel A) and in a cell exposed to 100 nM imetit (panel B), and illustrates the protocol used for these experiments. The $EC_{50}$ for imetit to activate the $H_3R$ is 2 nM (13).

In FIG. 1A, the cell was initially superfused with $Na^+$-Ringer solution (NaR), then with 20 mM $NH_4Cl$. Acute exposure to $NH_4Cl$ resulted in acidification of the cytosol to ~$pH_i$ 6.2 after its removal. In the absence of extracellular Na (0 Na), there was no measurable $pH_i$ recovery. With the re-introduction of extracellular $Na^+$ (NaR), $pH_i$ increased with intracellular alkalinization occurring at a rate of 0.094 $pH_i$ units/min (dotted line). The final $pH_i$, achieved in the cell shown in this trace, was higher than the starting $pH_i$ (6.8 vs. 6.6). This overshoot of the final $pH_i$ relative to the initial resting $pH_i$ was seen in the majority of control cells studied and is shown in the bar graph accompanying FIG. 1A. For the 221 control cells studied, the initial $pH_i$ was 6.69±0.01 and the final $pH_i$ was significantly higher at 6.76±0.01 (p<0.001).

Figure 1B:
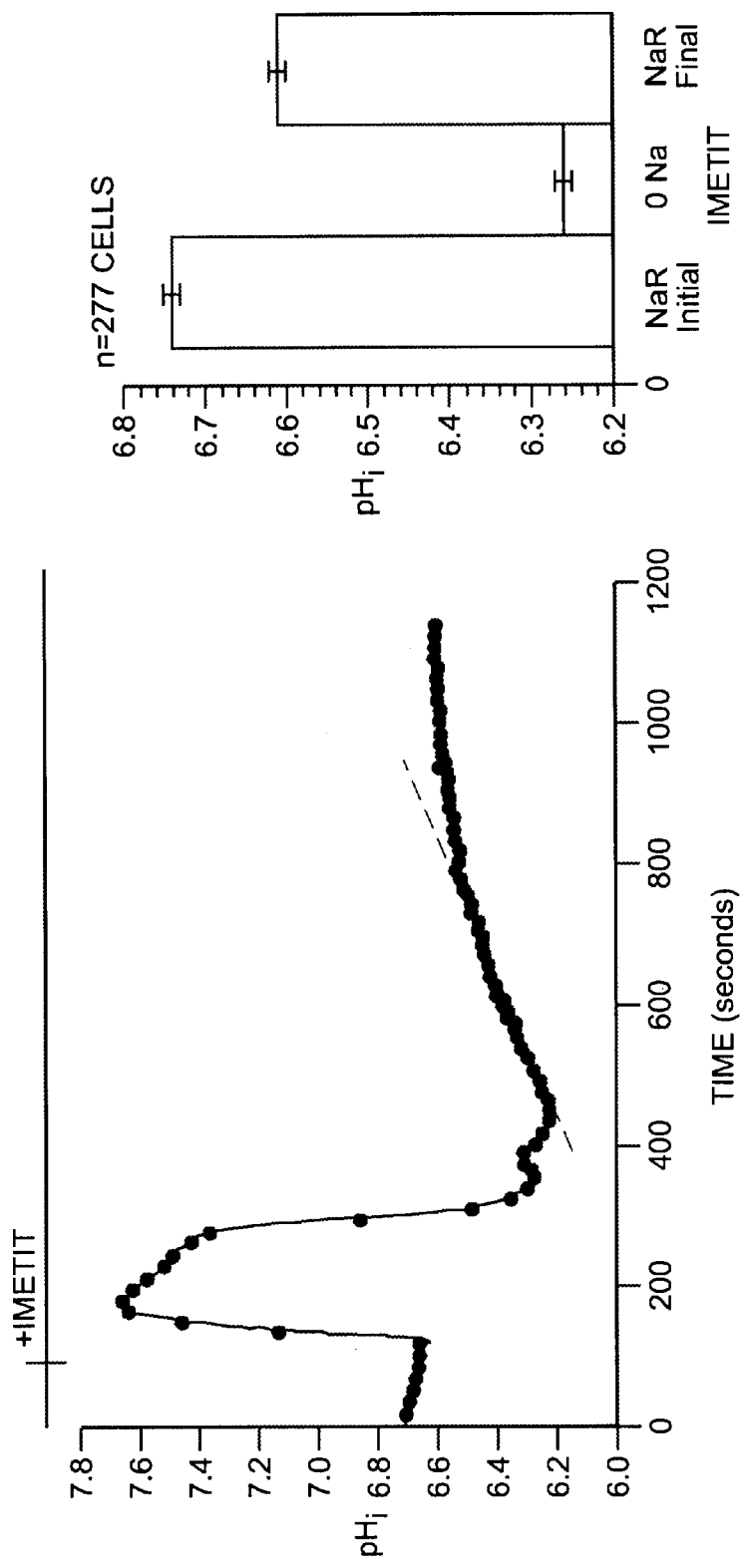
Figure 2A:
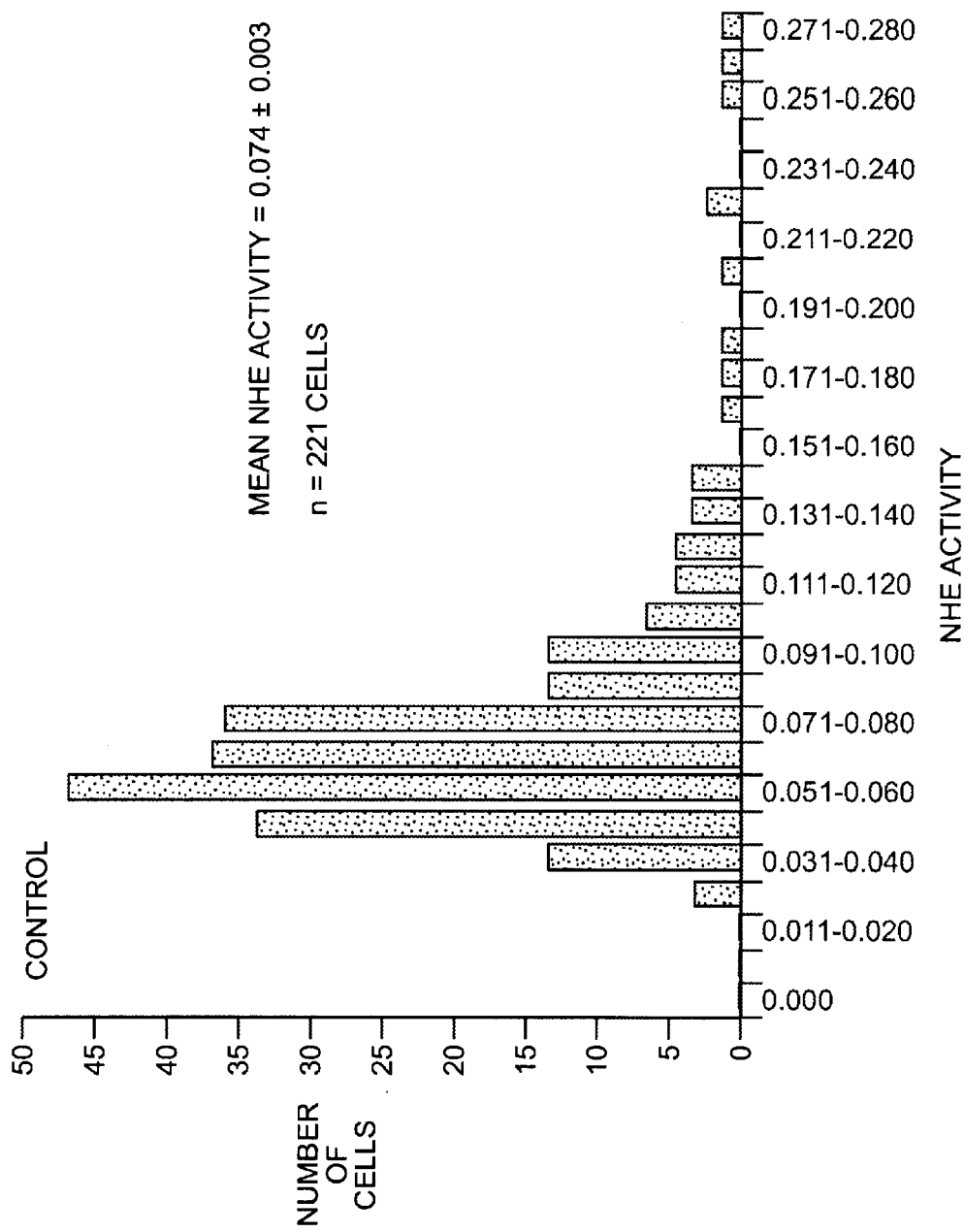
FIG. 2A. Histogram showing variability of $Na^+$-dependent $pH_i$ recovery rates (NHE activity) in control SKNMC-H₃ cells. The ordinates represent the number of cells and the abscissae the $Na^+$-dependent $pH_i$ recovery rates binned in 0.09 $pH_i$ unit/min increments. The FIGURE illustrates the variability of the response of 221 control cells studied from five coverslips.
Figure 2B:
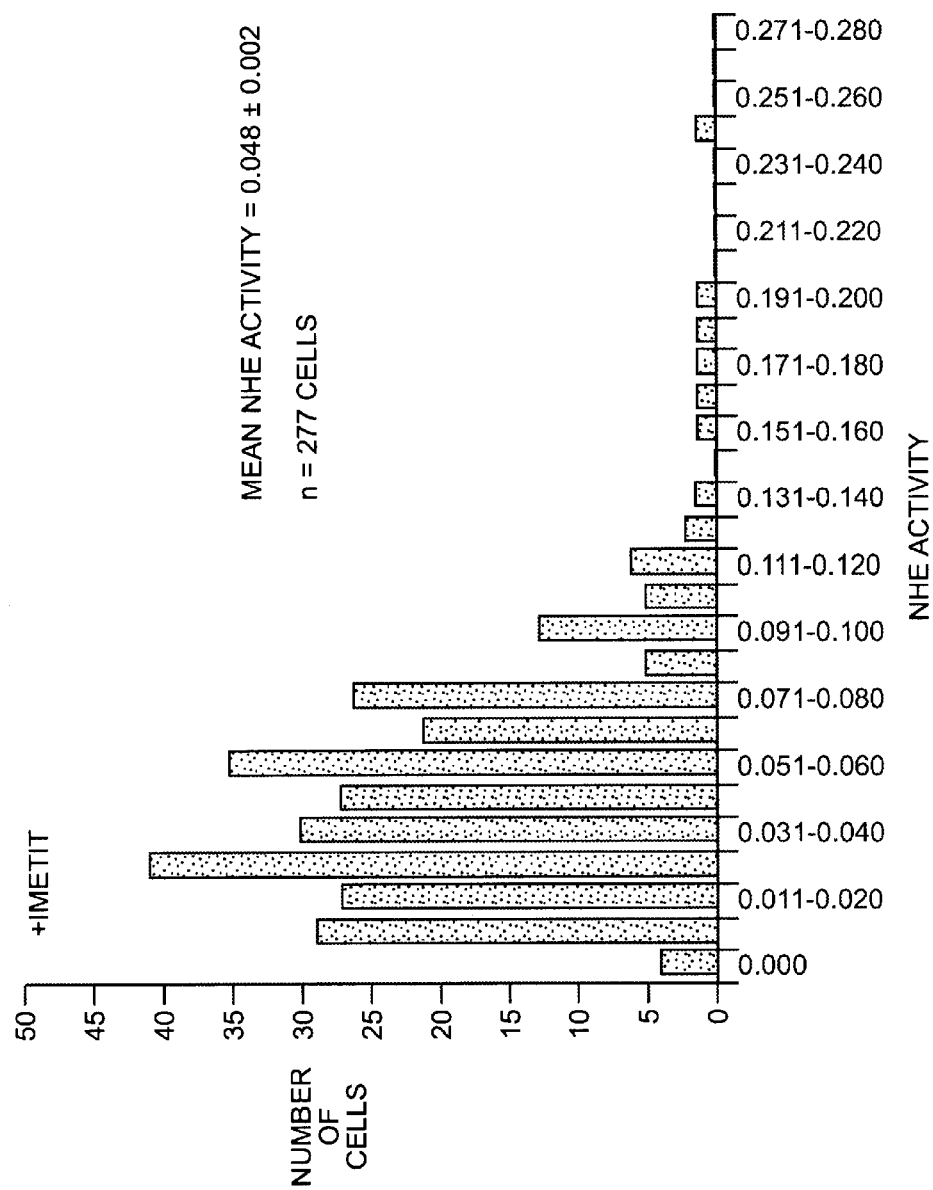
FIG. 2B. Histogram showing variability of $Na^+$-dependent $pH_i$ recovery rates (NHE activity) in imetit-treated SKNMC-H₃ cells. The ordinates represent the number of cells and the abscissae the $Na^+$-dependent $pH_i$ recovery rates binned in 0.09 $pH_i$ unit/min increments. The FIGURE illustrates the response of 227 cells from six coverslips exposed to imetit (at a concentration of 100 nM.
Figure 3:
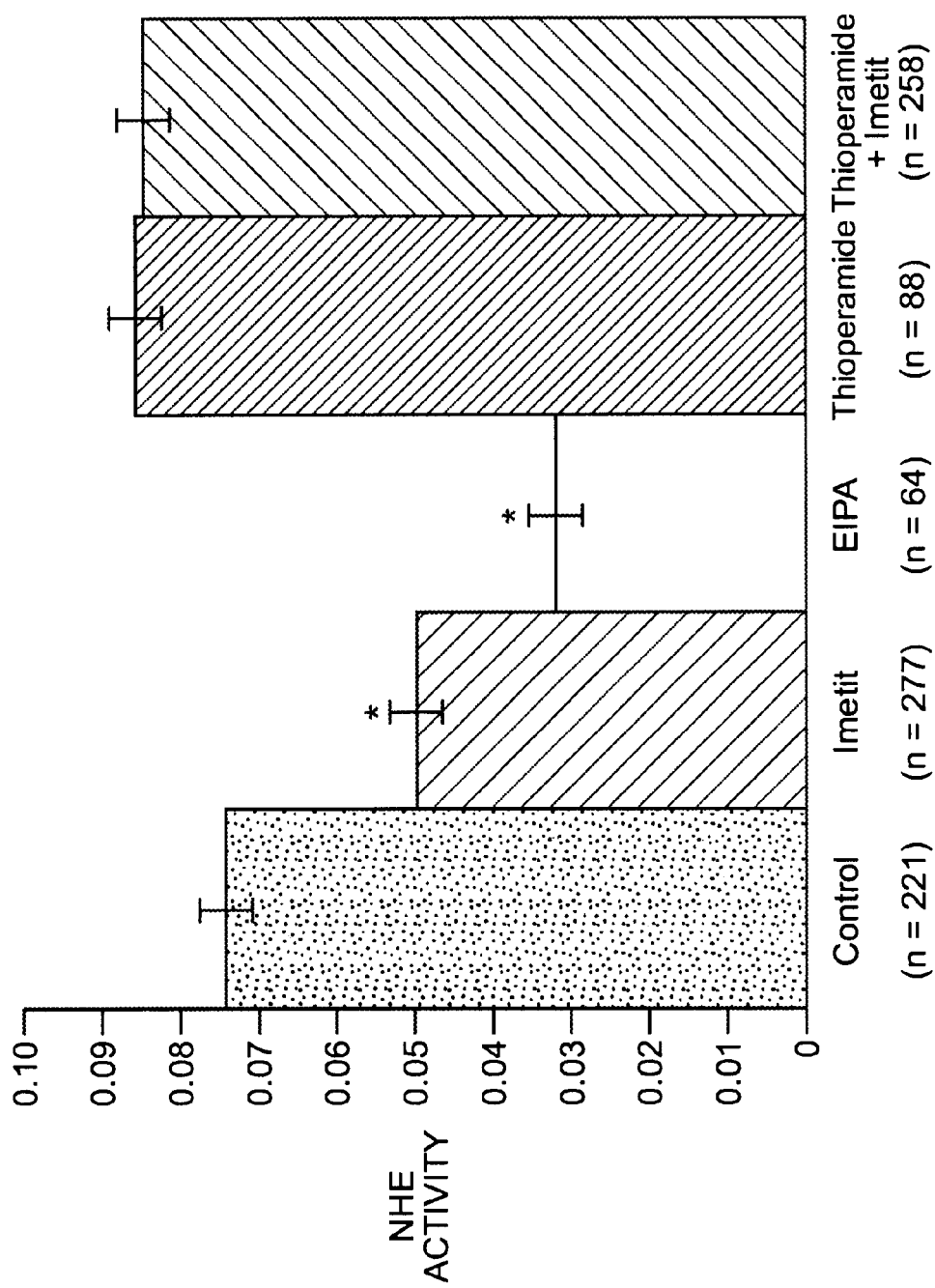
FIG. 3. Comparison of NHE activity in the absence and presence of imetit, EIPA, thioperamide, and imetit plus thioperamide in SKNMC-H₃ cells.

In FIG. 1B, imetit (100 nM) was present in the superfusate from the addition of $NH_4Cl$ until the end of the protocol as shown. Acute exposure to $NH_4Cl$ resulted in acidification of the cytosol to ~6.2 after its removal. In the absence of extracellular $Na^+$ (0 Na), there was no measurable $pH_i$ recovery. With the re-introduction of extracellular $Na^+$ (NaR), $pH_i$ started to increase with intracellular alkalinization occurring at a rate of 0.050 $pH_i$ units/min. The mean rate of $Na^+$-dependent $pH_i$ recovery was significantly less than that observed in the control cells (p<0.0001) (FIGS. 2 and 3). The final $pH_i$ achieved in the cell shown in this trace was lower than the starting $pH_i$ (6.7 vs. 6.5). This $pH_i$ undershoot relative to the starting $pH_i$, was seen in the majority of cells exposed to imetit, as shown in the bar graph of FIG. 1B. Unlike control cells, the final $pH_i$ of the 277 imetit-treated cells was significantly lower than the initial $pH_i$ (6.61±0.01 vs. 6.74±0.01; p<0.0001).

Overall, imetit significantly reduced the rate of $Na^+$-dependent $pH_i$ recovery (0.048±0.002, n=277 cells vs. 0.074±0.003 $pH_i$ units/min, n=221 cells; p<0.0001; see FIGS. 2 and 3).

In addition, imetit not only slowed the rate of NHE activity, but prevented the full recovery of $pH_i$. This is shown in the bar graphs of FIG. 1, where in the presence of imetit, the final $pH_i$ reached after re-introduction of $Na^+$ was significantly lower (6.61±0.01, n=277 cells) than the initial $pH_i$ (6.74±0.01, n=277 cells)(p<0.0001). In contrast, in the control cells, the final $pH_i$ was significantly higher (6.76±0.01, n=221 cells) than the initial $pH_i$ (6.69±0.01, n=221 cells)(p<0.001). Notably, the $pH_i$ measured right before $Na^+$ was reintroduced (0 Na $pH_i$) was the same in control and imetit-treated cells (control 6.23±0.01, n=221 cells and imetit-treated 6.26±0.01, n=277 cells). Thus the imetit-induced attenuation of NHE could not have resulted from a difference in $pH_i$ immediately preceding exchanger activation. Collectively, the results in FIG. 1 demonstrate that activation of $H_3R$ diminishes NHE activity and thus, the ability of the exchanger to extrude $H^+$.

Next, the variability in NHE activity of control and imetit-treated cultured cell populations was assayed. FIG. 2 is a histogram for the $pH_i$ recovery rates of individual cells (panel A: control; panel B: imetit-treated). The $Na^+$-dependent recovery rates are binned in increments of 0.09 $pH_i$ units/min. All of the cells exhibited a $Na^+$-dependent recovery response from the acid load. For the control cells (n-221), the rate of recovery ranged from 0.025 to 0.275 $pH_i$ units/min, with a mean of 0.074±0.002 $pH_i$ units/min. The recovery rate of imetit-treated cells (n=277) ranged from 0 to 0.198 $pH_i$ units/min, with a mean of 0.048±0.002 $pH_i$ units/min (p<0.0001). This difference in the distribution of NHE activity is clearly reflected in the imetit-induced leftward shift of the histogram (compare panels A and B). Indeed, 77% of the 277 imetit-treated cells exhibited rates lower than the mean control rate of 0.074 $pH_i$ units/min.

As shown in FIG. 3, the mean control $Na^+$-dependent $pH_i$ recovery rate or NHE activity ($pH_i$ units/min) is compared with rates measured in cells exposed to imetit (100 nM), EIPA (10 uM), thioperamide (300 nM), and thioperamide in combination with imetit. *Significantly different (P<0.0001) from control NHE activity. Values are means ±S.E.M and n refers to the number of cells studied. Imetit, thioperarnide, and EIPA were present in the superfusate from the $NH_4Cl$ pulse to the end of the experiment. In the experiments with imetit and thioperamide in combination, thioperamide was first introduced in the $NH_4Cl$ solution and 5 minutes later, imetit was added to the $Na^+$-free solution, for an additional 5 minutes, before the re-introduction of $Na^+$ into the superfusate.

FIG. 3 shows that the selective $H_3R$ antagonist thioperamide (300 nM) (KB 4 nM; (21)) did not significantly modify NHE activity, but abolished the imetit-induced NHE attenuation. This suggests that the effect of imetit results specifically from $H_3R$ activation. FIG. 3 also shows that the amiloride analog EIPA (10 uM), reduced the rate of $Na^+$-dependent intracellular alkalinization from 0.074 to 0.031 $pH_i$ units/min, confirming that the $Na^+$-dependent intracellular $pH_i$ recovery from the acid load is due to NHE. EIPA was significantly more effective than imetit in inhibiting NHE activity (50% vs 35% inhibition, p<0.001).

Figure 5:
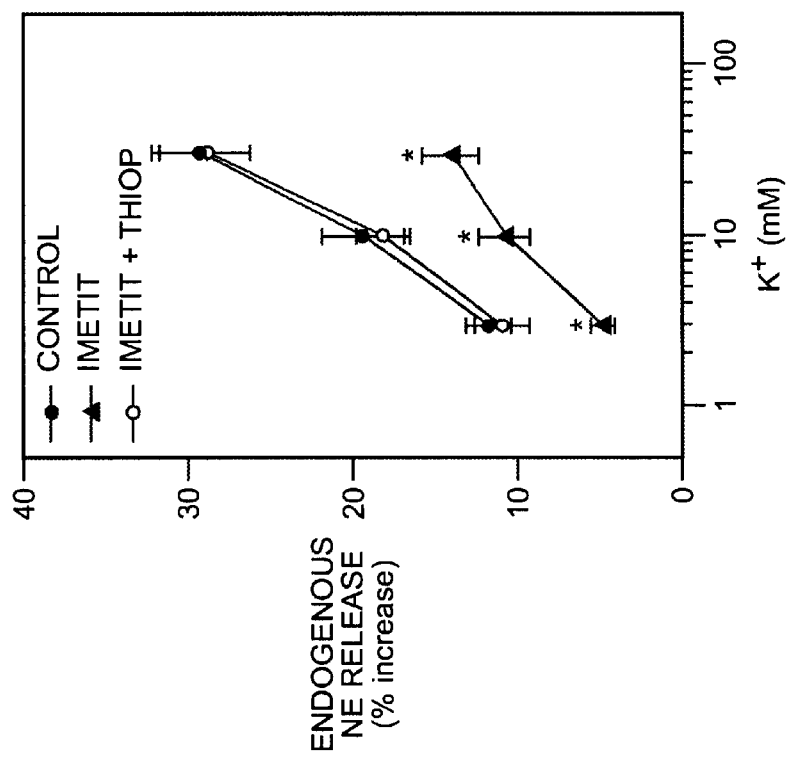
FIG. 5. Release of endogenous norepinephrine (NE) from guinea-pig heart synaptosomes by depolarization with 3–30 mM $K^+$ in the absence and presence of the selective $H_3R$ agonist imetit (100 nM), either alone or in combination with the selective $H_3R$ antagonist thioperamide (300 nM). Points represent mean increases in NE release above basal level (±SEM; n=8). Basal NE level was 1.14±0.01 pmol/mg of protein. *, P<0.05 from corresponding control NE level by unpaired t-test.
Figure 4:
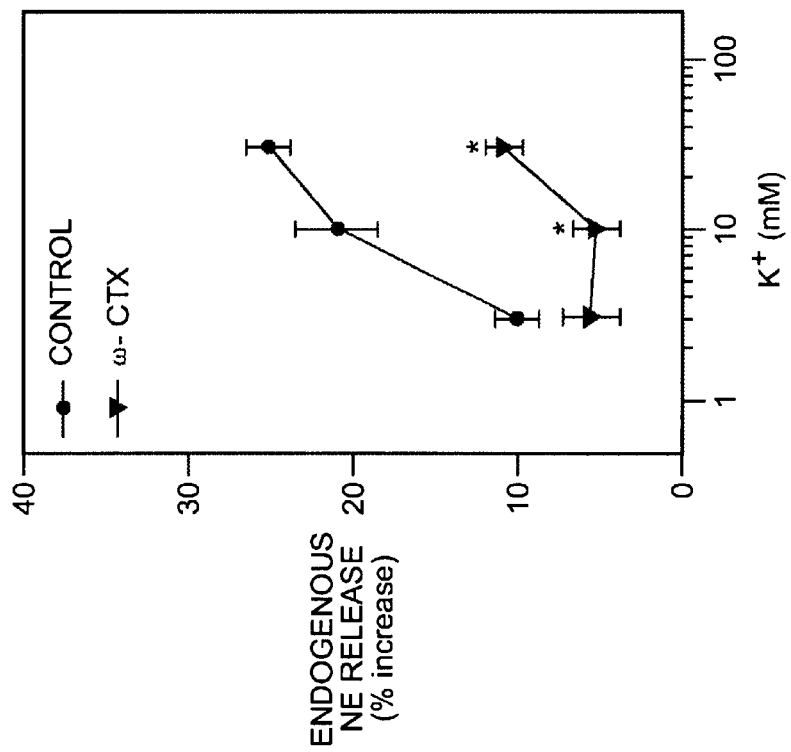
FIG. 4. Release of endogenous norepinephrine (NE) from guinea-pig heart synaptosomes by depolarization with 3–30 mM $K^+$ in the absence and presence of the selective N-type $Ca^{2+}$-channel inhibitor (o-conotoxin (100 $\mu M$). Points represent mean increases in NE release above basal level (±SEM; n=8). Basal NE level was 1.63±0.02 pmol/mg of protein. *, $P<0.05$ from corresponding control NE level by unpaired t-test.

Exocytosis of Endogenous NE from Cardiac Sympathetic Nerve Terminals:

Depolarization of cardiac synaptosomes with $K^+$ (3–30 mM) elicited a 10–30% increase in the release of endogenous NE (FIGS. 4 and 5). In the presence of the selective N-type $Ca^{2+}$-channel blocker ω-conotoxin (ω-CTX;100 nM), the concentration-response curve for the $K^+$-induced NE exocytosis was shifted markedly downwards (FIG. 4).

In the presence of the selective $H_3R$ agonist imetit (100 nM), the concentration-response curve for the $K^+$-induced exocytosis of endogenous NE was likewise significantly shifted downwards. This effect was prevented by the selective $H_3R$ antagonist thioperamide (300 nM) as shown in FIG. 5.

Figure 6B:
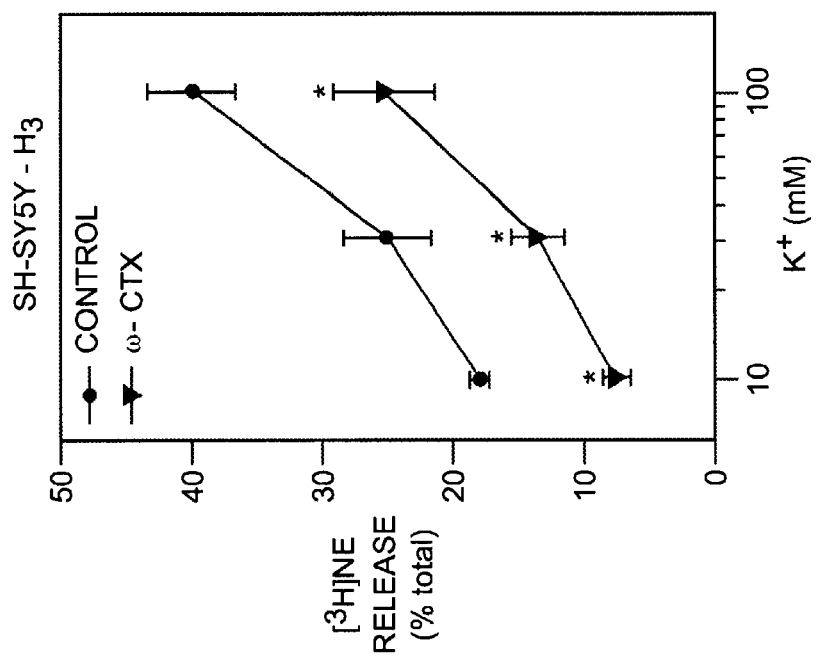
FIG. 6. Selective inhibition of N-type $Ca^{2+}$-channels with co-conotoxin (ω-CTX; 100 nM) attenuates both $Ca^{2+}$ influx and resulting exocytosis of tritiated NE in $K^+$-depolarized, cultured neuroblastoma cells. Upper panels: release of $[^3H]$ NE from parent SH-SY5Y (panel A) and $H_3R$-transfected SH-SY5Y (SH-SY5Y-$H_3$) cells (panel B), by depolarization with 10–100 mM $K^+$, in the absence and presence of ω-CTX (100 nM). Points represent mean $[^3H]NE$ release expressed as a percentage of total $[^3H]NE$ content (±SEM; n=3–5). *, P<0.05 from corresponding control $[^3H]NE$ level by unpaired t-test. Lower panels: peak $Ca_i$ concentration in SH-SY5Y (panel C) and SH-SY5Y-H3 cells (panel D) depolarized with 100 mM $K^+$ in the absence and presence of (O-CTX (100 nM). Bars represent means (±SEM) of 157 control and 87 co-CTX-treated SH-SY5Y cells (panel C), 232 control and 203 ω-CTX-treated SH-SY5Y-H3 cells (panel D). *, P<0.05 from corresponding control peak $Ca_i$ level by unpaired t-test.
Figure 6A:
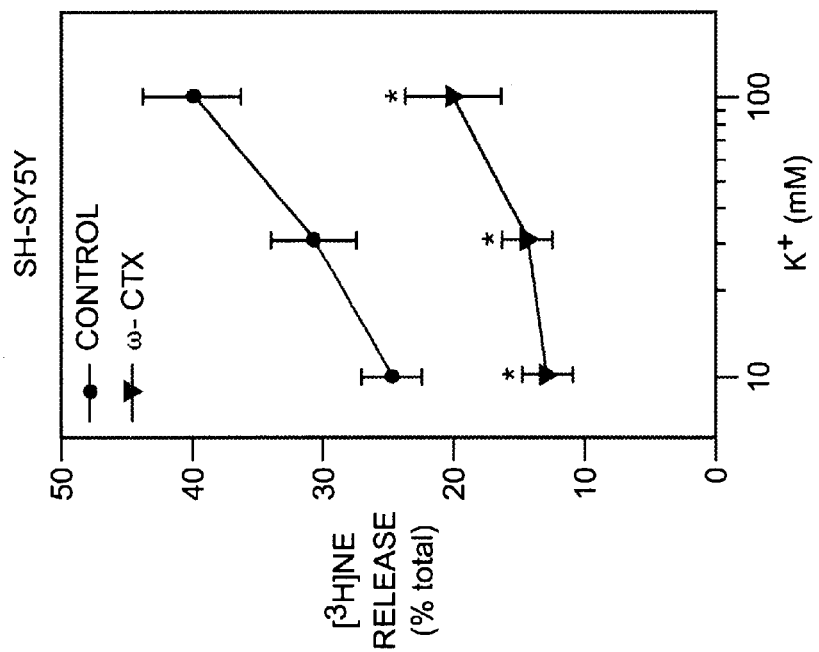
Figure 6D:
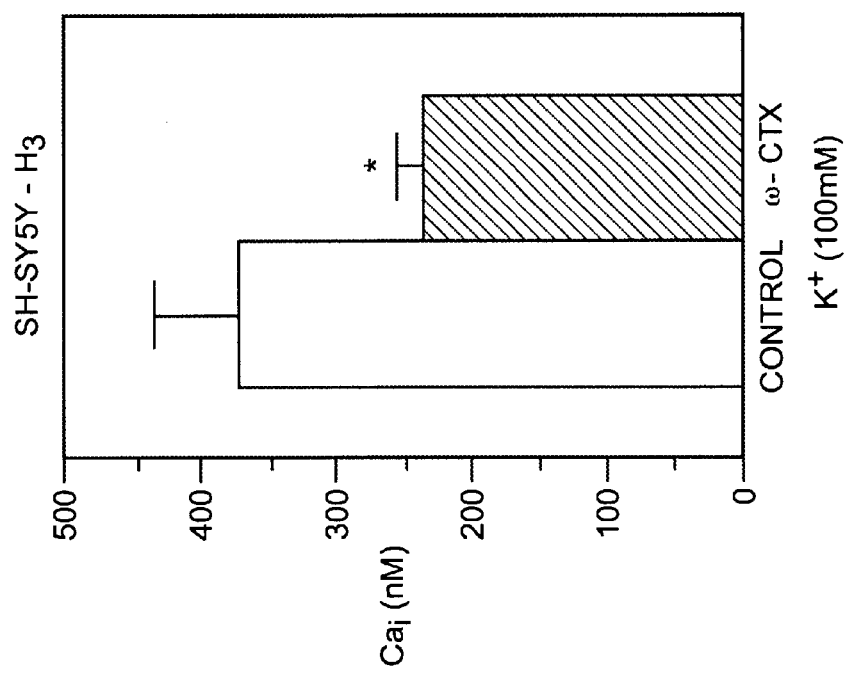
Figure 6C:
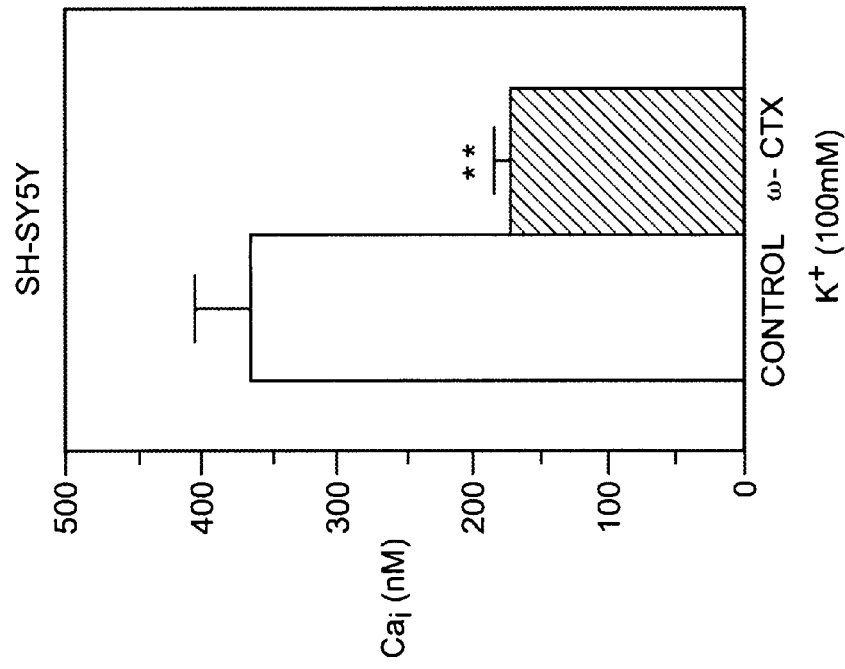
Figure 7B:
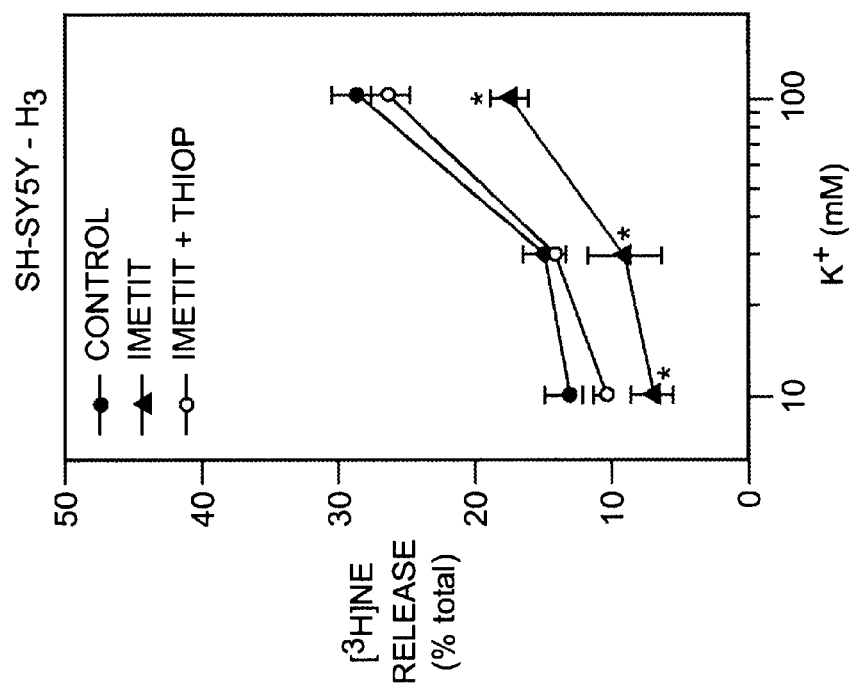
FIG. 7. Activation of $H_3R$ with the selective agonist imetit (100 nM) attenuates both $Ca^{2+}$ influx and resulting exocytosis of tritiated NE in $K^+$-depolarized, cultured neuroblastoma cells transfected with the $H_3R$ (SH-SY5Y–$H_3$; panels B and D). Parent SH-SY5Y cells fail to respond to imetit (panels A and C). Upper panels: release of $[^3H]NE$ from SH-SY5Y (panel A) and SH-SY5Y-$H_3$ cells (panel B), by depolarization with 10–100 mM $K^+$, in the absence and presence of imetit (100 nM), either alone or in combination with the selective $H_3R$ antagonist thioperamide (300 nM; panel B). Points represent mean [3H]NE release expressed as a percentage of total $[^3H]NE$ content (± SEM; n=3–7). *, P<0.05 from corresponding control $[^3]NE$ level by unpaired t-test. Lower panels: peak $Ca_i$ concentration in SH-SY5Y (panel C) and SH-SY5Y-$H_3$ cells (panel D) depolarized with 100 mM $K^+$ in the absence and presence of imetit ± thioperamide (panel D). Bars represent means (±SEM) of 157 control and 174 imetit-treated SH-SY5Y cells (panel C), 232 control, 197 imetit-treated, and 231 imetit+thioperamide-reated SH-SY5Y-$H_3$ cells (panel D). *, P<0.05 from corresponding control peak $Ca_i$ level by unpaired t-test.
Figure 7A:
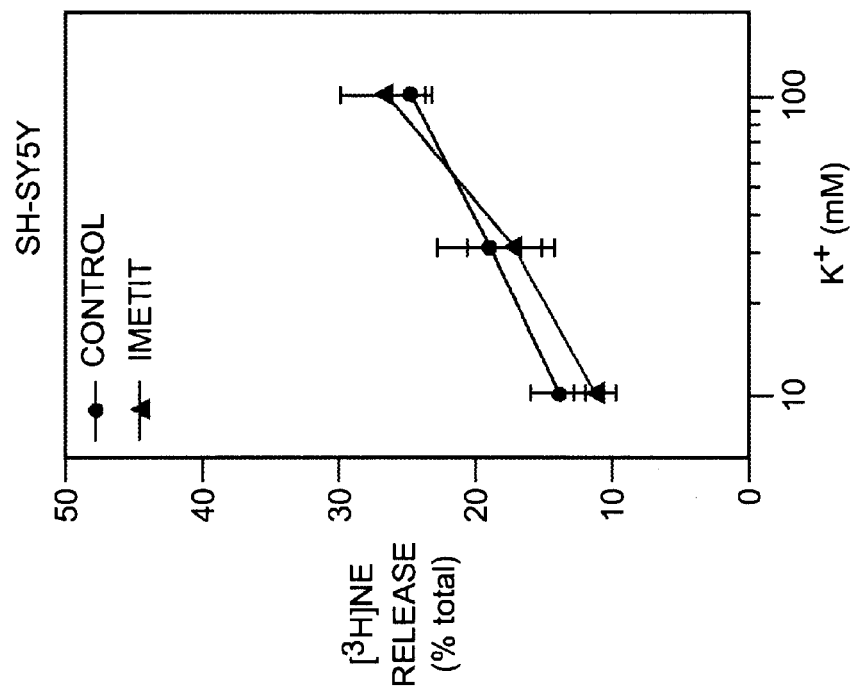

Exocytosis of Tritiated NE from Cultured Neuroblastoma Cells:

Depolarization of neuroblastoma cells SH-SY5Y and SH-SY5Y-H3 with $K^+$ (10–100 mM) elicited a concentration-dependent release of [$^3H$]NE (10–40% of stored [$^3H$]NE; FIGS. 6A–B and 7AB). In the presence of ω-CTX (100 nM), the concentration-response curve for the $K^+$-induced exocytosis of [$^3H$]NE was shifted markedly downwards in both SH-SY5Y and SH-SY5Y-H3 cells (FIGS. 6A and B).

In contrast, in the presence of the selective $H_3R$ agonist imetit (100 nM), the concentration-response curve for the $K^+$-induced exocytosis of [$^3H$]NE was significantly shifted downwards only in neuroblastoma cells transfected with the $H_3R$, but not in the non-transfected parent cells (compare panels A and B in FIG. 7). When present, the effect of imetit was prevented by the selective $H_3R$ antagonist thioperamide (300 nM) as shown in FIG. 7B.

$Ca^{2+}$ Influx in Cultured Neuroblastoma Cells:

To test directly the hypothesis that $H_3R$ activation diminishes $Ca^{2+}$ influx, we measured $Ca_i$ in response to $K^+$-induced membrane depolarization in parent SH-SY5Y cells and SH-SY5Y-$H_3$ cells loaded with the $Ca_i$ indicator Fura-2. FIG. 8 shows representative $Ca_i$ responses at the individual cell level in the parent (panels A and B) and $H_3R$-transfected neuroblastoma cells (panels C, D, and E). As shown for both SH-SY5Y and SH-SY5Y-H3 cells, exposure to high extracellular $K^+$ (100 mM), led to a rapid increase in $Ca_i$ followed by a rapid return to initial levels (FIGS. 5A and C).

Figure 7D:
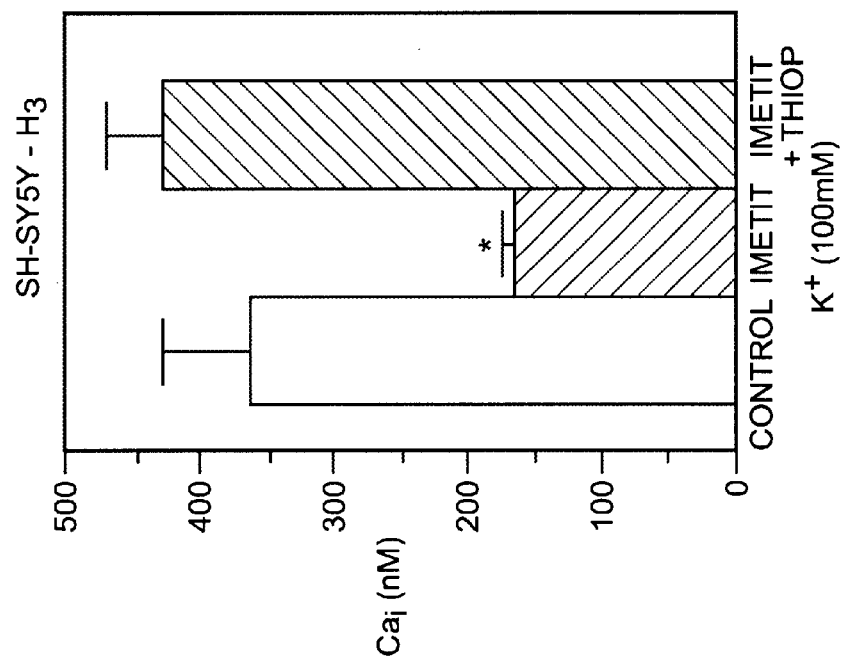
Figure 7C:
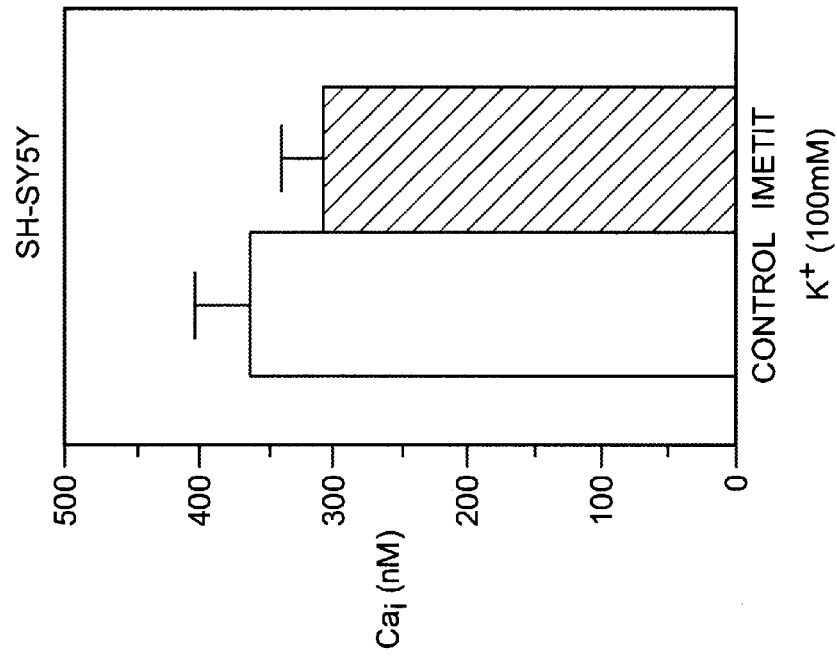
Figure 8A:
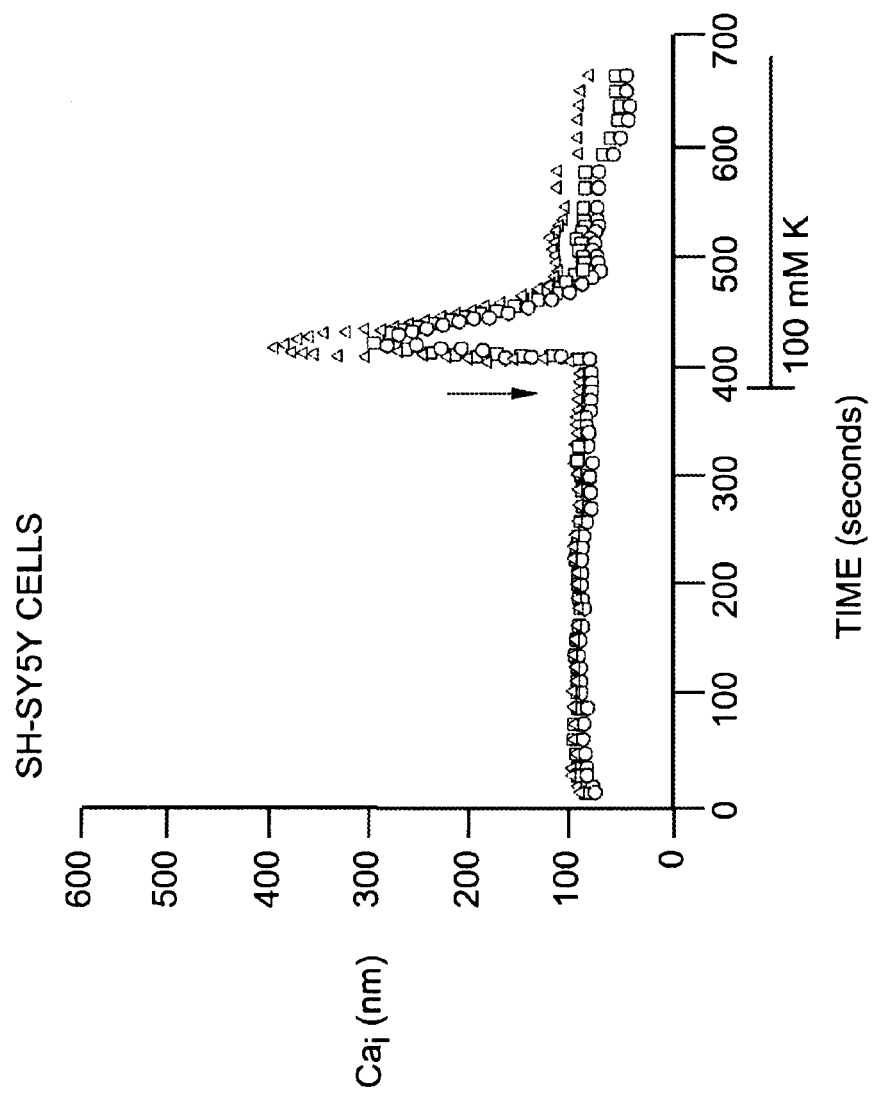
FIG. 8. $Ca_i$ transients in K+-depolarized SH-SY5Y (panel A), and SH-SY5Y-$H_3$ (panel C), cultured neuroblatoma cells. Ordinates represent the $Ca_i$ concentration determined by intracellular calibration of the Fura-2 signal emitted from 3 individual representative cells in each panel. All cells were initially superfused with HBS Na Ringer's solution and subsequently exposed to 100 mM $K^+$ in the absence or presence of the pharmacological agents indicated. Note that the selective $H_3R$ agonist imetit fails to affect $Ca_i$ transients in SH-SY5Y (panel B) but markedly suppresses $Ca_i$ transients in SH-SY5Y-$H_3$ cells (panel D), an effect which is prevented by the selective $H_3R$ antagonist thioperamide (panel E).
Figure 8B:
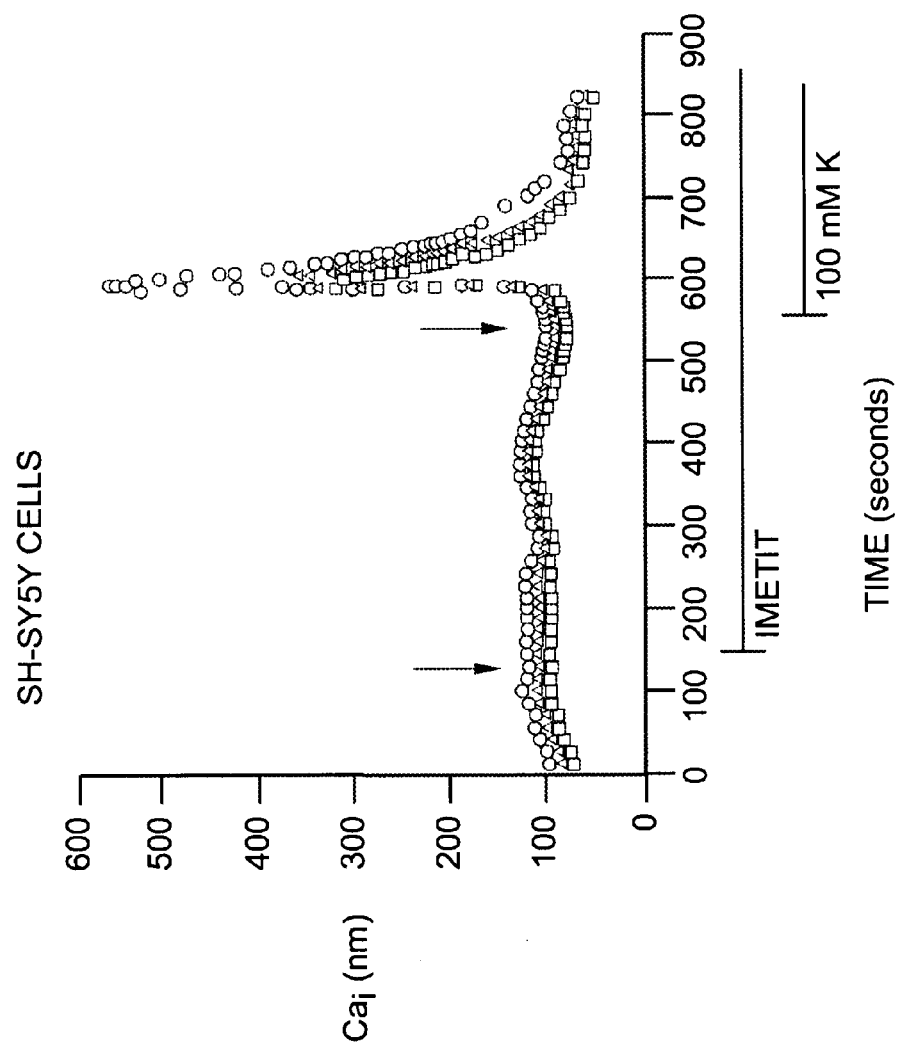
Figure 8C:
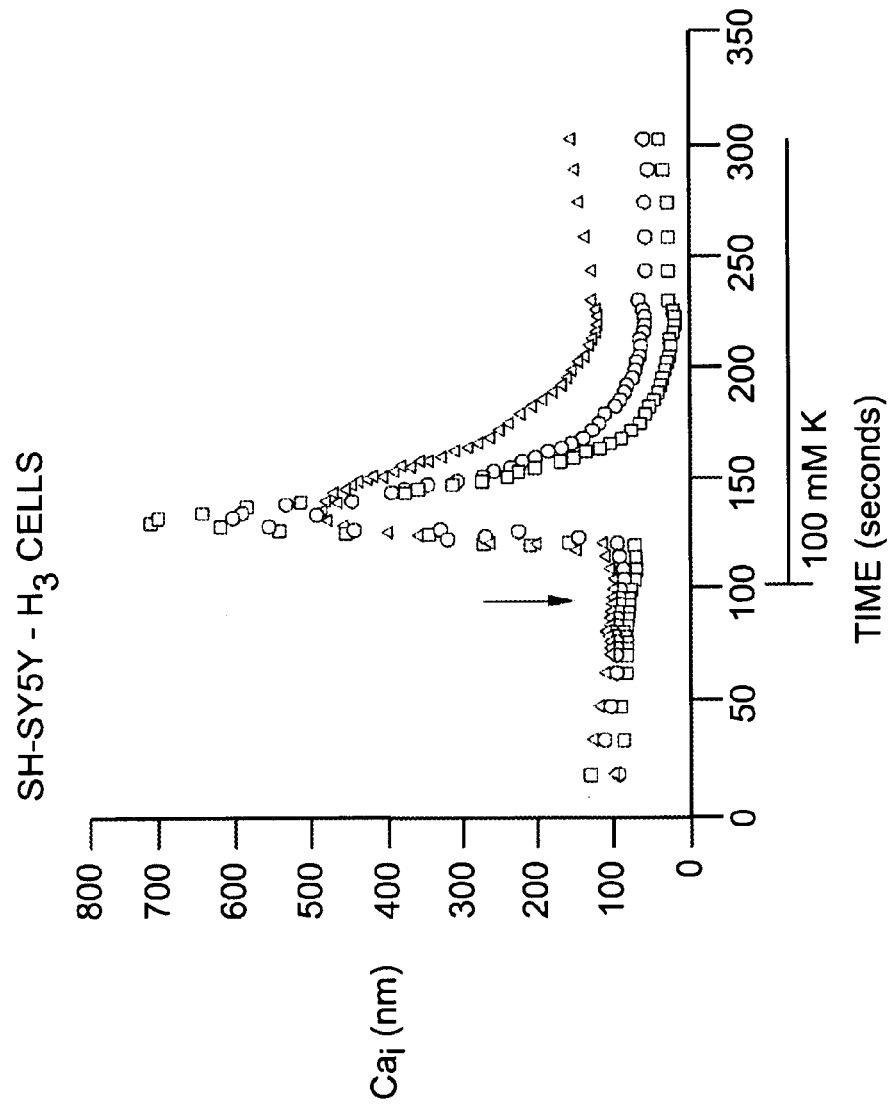
Figure 8D:
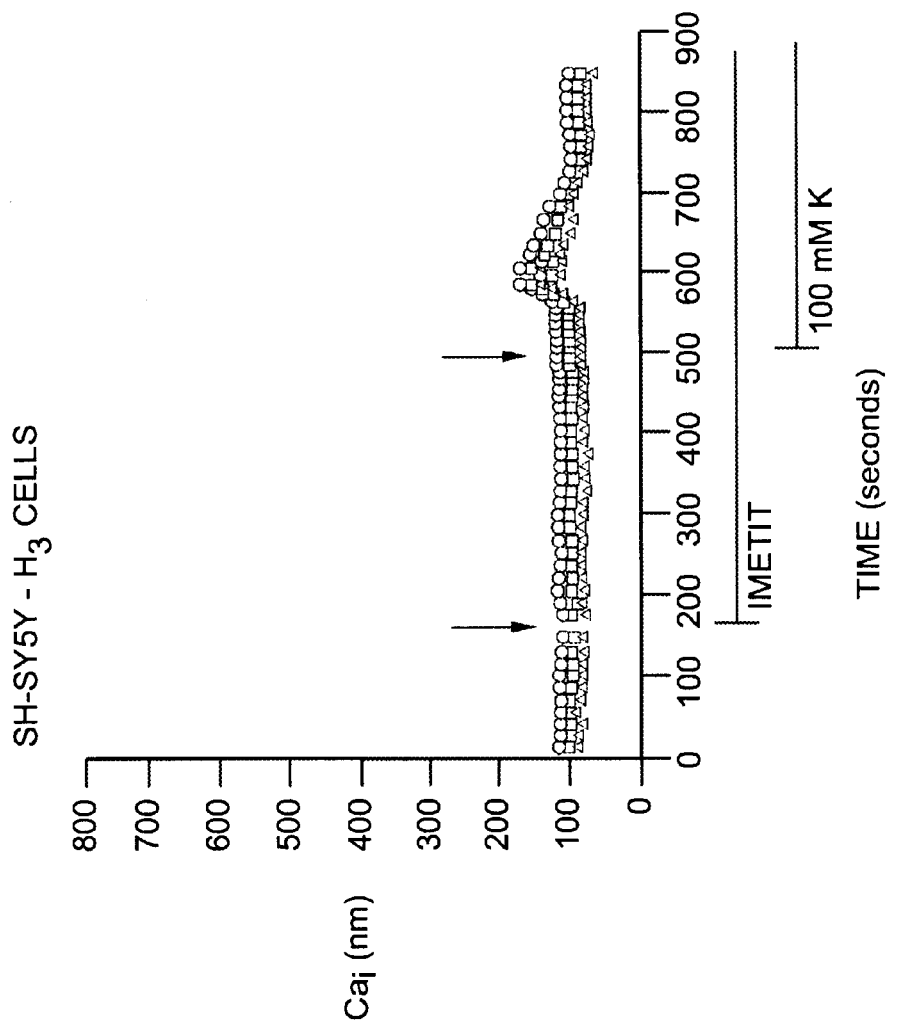
Figure 8E:
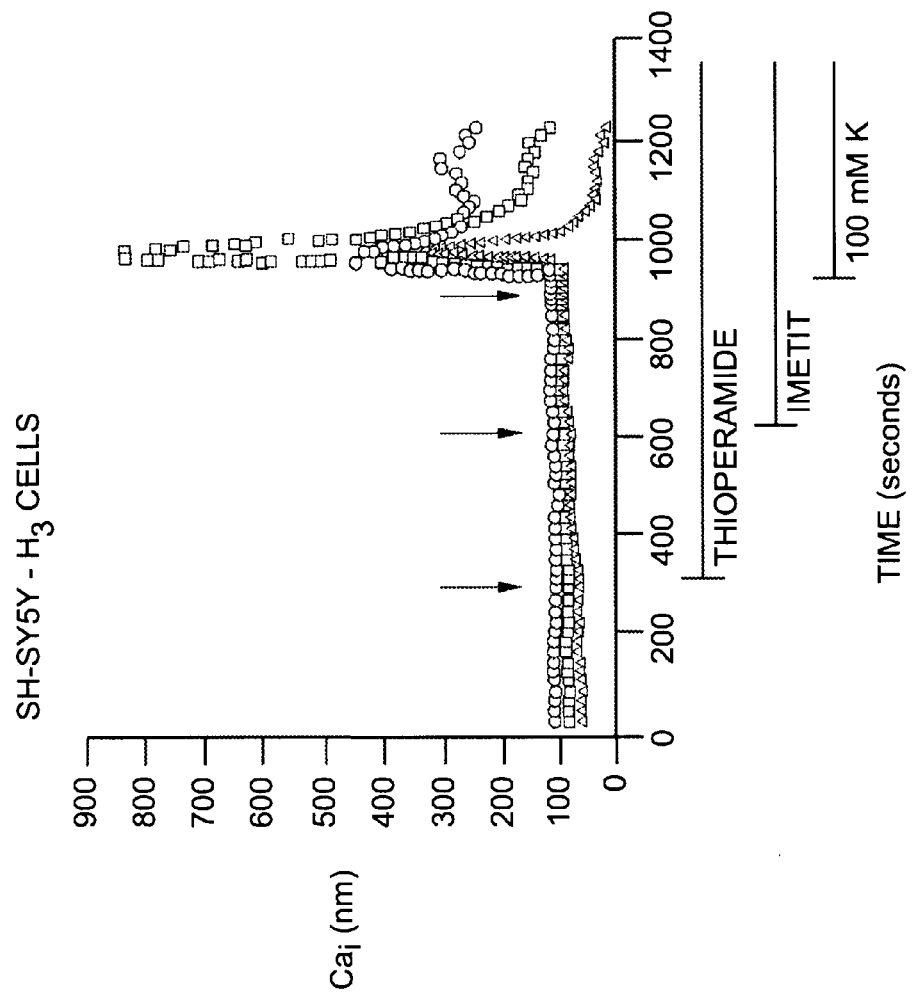

In the presence of the selective $H_3R$ agonist imetit (100 nM), $K^+$-elicited $Ca^{2+}$ transients were markedly depressed in the SH-SY5Y-H3, but not in the SH-SY5Y cells (compare panels B and D in FIG. 8). The response to imetit was prevented by the selective $H_3R$ antagonist thioperamide (300 nM; FIG. 8E). A quantitative evaluation of the effects of imetit is shown in FIGS. 7C and 7D. Whereas imetit caused a 55% decrease in the peak $Ca_i$ concentration elicited by 100 mM $K^+$ in the $H_3R$-transfected cells (FIG. 7D), it failed to affect peak $Ca_i$ concentration in the non-transfected cells (FIG. 7C). The imetit-induced depression of the rise in $Ca_i$ concentration was completely prevented by the selective $H_3R$ antagonist thioperamide (FIG. 7D).

Relationship Between $Ca_1$ and NE Exocytosis:

The relationship between $Ca_i$ concentration and NE release is shown in FIG. 6. When neuroblastoma cells were depolarized with $K^+$, the increase in peak $Ca_i$ concentration was markedly attenuated in the presence of ω-CTX (100 nM) in both parent and $H_3R$-transfected cells (FIGS. 6C and 6D). In both cells, this decrease in $Ca_i$ was associated with a marked decrease in [$^3H$]NE release (FIGS. 6A and 6B). A decrease in endogenous NE release was also observed in sympathetic nerve endings in the presence of ω-CTX (100 nM; See FIG. 4).

The same association between $Ca_i$ and NE release was observed also in cells depolarized with $K^+$ in the absence and presence of $H_3R$ ligands. When imetit was used in parent SH-SY5Y cells, the increases in $Ca_i$ and NE release in response to K were unaffected (FIGS. 7C and 7A). In contrast, when imetit was used in SH-SY5Y-H3 cells, the marked decrease in peak $Ca_i$ concentration was associated with a marked attenuation in NE release. Moreover, in the presence of thioperamide, the abolition of the effect of imetit on $Ca_i$ was associated with a restoration of NE release (FIGS. 7D and 7B).

Discussion

The results of the first study demonstrate that $H_3R$ activation in human neuroblastoma cells, stably transfected with $H_3$ cDNA, inhibits NHE activity. Cultured neuroblastoma cells are a model of cardiac adrenergic nerve endings (22). Thus, the present results provide a link between $H_3R$ and NHE, which may limit the excessive release of NE during protracted myocardial ischemia.

FIG. 1 shows that $H_3R$ activation is linked to a decrease in NHE activity, and that the amiloride derivative EIPA markedly inhibits the rate of $Na^+$-dependent intracellular alkalinization in SKNMC-$H_3$ cells (FIG. 3). The latter result proves that the recovery from $NH_4Cl$-induced acidosis is due to NHE activation (20). The selective $H_3R$ agonist imetit (13), inhibited the rate of recovery from an acid load, and the action of imetit was blocked by the selective $H_3R$ antagonist thioperamide (19). These results indicate that $H_3R$ activation triggers a decrease in NHE activity.

Intracellular pH plays an important role in modulating NHE activity (14) and differences in $pH_i$ could account for variability in the rate of $Na^+/H^+$ exchange. But the $pH_i$ measured in control and imetit-treated cells, when $Na^+$ was re-introduced to the superfusate after the $NH_4Cl$ pulse, was similar for both (~$pH_i$ 6.2, FIG. 1). Hence, $H_3R$ activation modifies NHE activity via a mechanism other than a change in $pH_i$. $H_3R$ activation also limits the $pH_i$ range over which NHE functions, because the $Na^+$-dependent $pH_i$ recovery from the acid load was less complete in imetit-treated cells than in controls. Thus, once $Na^+$ had been reintroduced to the superfusate and NHE activated, the final $pH_i$ reached in the cell was significantly lower in the imetit-treated cells than in controls (FIG. 1). This represents a compensatory effort by the cell to curb excess accumulation of intracellular $Na^+$, which translates into a potentially beneficial mechanism, since "carrier-mediated" NE release and intracellular acidosis are both attenuated.

FIG. 2 provides additional evidence linking $H_3R$ activation to diminished NHE activity. Indeed, by plotting the $Na^+$-dependent recovery rates in response to an acid load (NHE activity) against the number of cells displaying such a rate, it becomes evident that imetit-treated cells exhibit a markedly different distribution than control cells, with a marked shift toward lower NHE rates.

These findings highlight the importance of presynaptic $H_3R$ as negative modulators of excessive NE release, either through inhibition of exocytosis and/or inhibition of carrier mediated NE release in protracted myocardial ischemia, and their coupling to neuronal NHE. Due to their very high affinity for histamine ($K_D$=5 nM), in comparison with the much lower affinity of $H_1R$ and $H_2R$ ($K_D$~10 μM) (21), $H_3R$ are easily activated in myocardial ischemia by histamine released from mast cells juxtaposed to adrenergic nerve endings (11). Thus, these findings advocate a protective role for endogenous cardiac histamine in myocardial ischemia and a rationale for the use of selective $H_3R$ agonists to alleviate cardiac dysfunctions, particularly cardiac dysfunctions associated with ischemia.

The present invention also demonstrates that $H_3R$ activation inhibits NE release by diminishing $Ca_i$ in sympathetic nerve terminals (i.e., cardiac synaptosomes) expressing native H$_3$R (reference 25) and in a human neuroblastoma cell line (SH-SY5Y; reference 27), stably transfected with the H$_3$R cDNA (SH-SY5Y-H$_3$). The results demonstrate that the attenuation of NE exocytosis caused by activation of H$_3$R is associated with a marked decrease in Ca$_i$ concentration and this in turn is secondary to a decreased Ca$^{2+}$ influx into sympathetic nerve terminals.

The present invention is further supported by the findings that: (a) ω-CTX, which is known to impede Ca$^{2+}$ influx via N-type channels (8), markedly reduces the increase in Ca$_i$ in response to membrane depolarization with 100 mM K$^+$ in both parent and H$_3$R-transfected SH-SY5Y neuroblastoma cells; (b) in association with the decrease in Ca$_i$, ω-CTX also greatly attenuates the exocytosis of tritiated NE from both SH-SY5Y and SH-SY5Y-H$_3$ cells, and of endogenous NE from cardiac synaptosomes; (c ) similar to ω-CTX, H$_3$R activation with the selective H$_3$R agonist imetit (reference 13) markedly reduces the increase in Ca$_i$ in response to high K$^+$, a response that is prevented by the selective H$_3$R antagonist thioperamide (reference 19); (d) in association with the decrease in Ca$_i$, imetit also greatly attenuates the exocytosis of tritiated NE from SH-SY5Y-H$_3$ cells, and of endogenous NE from cardiac synaptosomes; (e) in sharp contrast, imetit affects neither the Ca$_i$ response nor the exocytosis of NE in parent SH-SY5Y cells, demonstrating not only that H$_3$R expression is a prerequisite for a decrease in Ca$_i$ in response to imetit, but also linking the magnitude of the increase in Ca$_i$ to the extent of NE exocytosis.

SH-SY5Y was chosen as the experimental cell line because this neuroblastoma cell line derived from the sympathetic nervous system expresses several properties of mature sympathetic neurons (reference 27). In addition, the present findings in neuroblastoma cells were strengthened by their similarity to the findings obtained in native cardiac sympathetic terminals. Indeed, all these responses were found to be equivalent in both neuroblastoma cells and cardiac sympathetic terminals.

The present discovery that H$_3$R-activation results in a decrease in axoplasmic Ca$^{2+}$ concentration, due to an impaired entrance of Ca$^{2+}$ through voltage-gated ion channels, pertains not only to cardiac physiology, but also to pathological conditions, such as acute myocardial ischemia, characterized by exaggerated NE exocytosis (reference 11) (4). Because excess NE release can trigger severe arrhythmias and sudden cardiac death, negative modulation of NE release in a patient by administration of an H$_3$R agonist offers a novel therapeutic approach to myocardial ischemia.

REFERENCES

1. Schomig, A., Richardt, G. & Kurz, T. (1995) Herz 20, 169–186.
2. Braunwald, E. & Sobel, B. E. (1988) in Heart Disease, a textbook of cardiovascular medicine, ed. Braunwald, E. (W.B.Saunders, Philadelphia), pp. 1191–1221.
3. Airaksinen, K. E. (1999) Ann. Med. 31, 240–245.
4. Smith, N.C. E. & Levi, R. (1999) J. Pharmacol. Exp. Ther. 291, 456–463.
5. Imamura, M., Lander, H. M. & Levi, R. (1996) Circ. Res. 78, 475–481.
6. Hatta, E., Yasuda, K. & Levi, R. (1997) J Pharmacol. Exp. Ther. 283, 494–500.
7. Arrang, J. M., Garbarg, M. & Schwartz, J. C. (1983) Nature 302, 832–837.
8. Endou, M., Poli, E. & Levi, R. (1994) J. Pharmacol. Exp. Ther. 269, 221–229.
9. Imamura, M., Poli, E., Omoniyi, A. T. & Levi, R. (1994) J Pharmacol. Exp. Ther. 271, 1259–1266.
10. Imamura, M., Seyedi, N., Lander, H. M. & Levi, R. (1995) Circ. Res. 77, 206–210.
11. Levi, R. & Smith, N.C. E. (2000) J. Pharmacol. Exp. Ther. 292, 825–830.
12. Lovenberg, T. W., Roland, B. L., Wilson, S. J., Jiang, X., Pyati, J., Huvar, A., Jackson, M. R. & Erlander, M. G. (1999) Mol. Pharmacol. 55, 1101–1107.
13. Garbarg, M., Arrang, J. M., Rouleau, A., Ligneau, X., Tuong, M. D., Schwartz, J. C. & Ganellin, C. R. (1992) J. Pharmacol. Exp. Ther. 263, 304–310.
14. Aronson, P. S., Nee, J. & Suhm, M. A. (1982) Nature 299, 161–163.
15. Cardone, M. H., Smith, B. L., Mennitt, P. A., Mochly-Rosen, D., Silver, R. B. & Mostov, K. E. (1996) J. Cell Biol. 133, 997–1005.
16. Silver, R. B. (1998) Methods Cell Biol. 56, 237–251.
17. Thomas, J. A., Buchsbaum, R. N., Zimniak, A. & Racker, E. (1979) Biochemistry 18, 2210–2218.
18. Silver, R. B., Choe, H. & Frindt, G. (1998) Am. J Physiol 275, F94–102.
19. Arrang, J. M., Garbarg, M., Lancelot, J. C., Lecomte, J. M., Pollard, H., Robba, M., Schunack, W. & Schwartz, J. C. (1987) Nature 327, 117–123.
20. Vigne, P., Frelin, C., Cragoe, E. J., Jr. & Lazdunski, M. (1983) Biochem. Biophys. Res. Commun. 116, 86–90.
21. Hill, S. J., Ganellin, C. R., Timmerman, H., Schwartz, J. C., Shankley, N. P., Young, J. M., Schunack, W., Levi, R. & Haas, H. L. (1997) Pharmacol. Rev. 49, 253–278.
22. Vaughan, P. F., Peers, C. & Walker, J. H. (1995) Gen. Pharmacol. 26, 1191–1201.
23. Mazenot, C., Durand, A., Ribuot, C., Demenge, P. and Godin-Ribuot, D. Fundam. Clin. Pharmacol. 1999, 13(4): 455–60.
24. Leurs, R., Hoffmann, M., Wieland, K. & Timmerman, H. (2000) Trends Pharmacol Sci 21, 11–12.
25. Seyedi, N., Win, T., Lander, H. M. & Levi, R. (1997) Circ. Res. 81, 774–784.
26. Sher, E., Biancardi, E., Passafaro, M. & Clementi, F. (1991) FASEB J 5, 2677–2683.
27. Vaughan, P. F., Peers, C. & Walker, J. H. (1995) Gen. Pharmacol. 26, 1191–1201.
28. Markwell, M. A., Haas, S. M., Bieber, L. L. & Tolbert, N. E. (1978) Anal. Biochem. 87, 206–210.
29. Murphy, N. P., Ball, S. G. & Vaughan, P. F. (1991) J Neurochem. 56, 1810–1815.
30. Lovenberg, T. W., Pyati, J., Chang, H., Wilson, S. J. & Erlander, M. G. (2000) J. Pharmacol. Exp. Ther. 293, 771–778.
31. Grynkiewicz, G., Poenie, M. & Tsien, R. Y. (1985) J. Biol. Chem. 260, 3440–3450.

We claim:

1. A method for reducing cardiac dysfunctions in a human in need thereof wherein the cardiac dysfunction is due to a patholoaical excess of noreninephrine release, the method comprising a administering to the human an effective amount of a selective histamine H$_3$ receptor agonist.

2. The method according to claim 1, wherein the cardiac dysfunction is associated with myocardial ischemia or myocardial infarction.

3. The method according to claim 1, wherein the cardiac dysfunction is arrhythmia, fibrillation, platelet activation and aggregation, thrombus formation, coronary spasm, sudden cardiac death or cardiac failure.

4. The method according to claim 1, wherein the selective histamine H$_3$ receptor agonist is R-(α)-methylhistamine, imetit, immepip, immepyr, 4-(1H-4-imidazolylmethylene) 1 methylpiperidine, S-α-chloromethylhistarnine, cyclopropyl-histamine, SKF 91606, Sch 50971, VUF 4864.

5. The method according to claim 1, wherein the selective histamine $H_3$ receptor agonist is administered after the onset of myocardial ischemia and/or myocardial infarction.

6. The method according to claim 1, wherein the selective histamine $H_3$ receptor agonist does not act on the central nervous system.

7. The method according to claim 1, wherein the selective histamine $H_3$ receptor agonist does not cross the blood brain barrier.

8. The method according to claim 1, wherein the histamine $H_3$ receptor is on a cardiac sympathetic nerve ending.

9. The method according to claim 1, wherein the histamine $H_3$ receptor agonist reduces norepinephrine release from a cardiac sympathetic nerve ending.

10. The method according to claim 1, wherein the reduction in norepinephrine release is specifically antagonized by an $H_3R$ antagonist.

11. The method according to claim 1, wherein the $H_3R$ antagonist is Thioperamide or Clobenpropit.

12. The method according to claim 1, wherein the histamine $H_3$ receptor agonist inhibits the $Na^+H^+$exchanger.

13. The method according to claim 12, wherein the histamine $H_3$ receptor agonist inhibits the $Na^+H^+$exchanger on a cardiac sympathetic nerve ending.

14. The method according to claim 1, wherein the histamine $H_3$ receptor agonist modulates the concentration of intracellular sodium.

15. The method according to claim 1, wherein the histamine $H_3$ receptor agonist modulates the concentration of intracellular calcium.

16. The method according to claim 15, wherein the histamine $H_3$ receptor agonist modulates the concentration of intracellular calcium by inhibiting the activity of an N-type Ca2+channel.

17. The method according to claim 1, wherein the histamine $H_3$ receptor agonist is delivered in combination with at least one other agent in the treatment of cardiac dysfunction.

18. The method according to claim 17, wherein the other agent is one or more of the following: β-blocker, a $Ca^{++}$-channel blocker, an anti-arrhythmic, an ACE inhibitor and an angiotensin receptor antagonist.

19. A method for inhibiting the $Na^+H^+$exchanger in a human having a cardiac dysfunction, the method comprising administering to the human an effective amount of a selective histamine $H^3$ receptor agonist.

20. The method according to claim 19, wherein the cardiac dysfunction is myocardial ischemia or myocardial infarction.

21. The method according to claim 19, wherein the cardiac dysfunction is arrhythmia, fibrillation, platelet activation and aggregation, thrombus formation, coronary spasm, sudden cardiac death or cardiac failure.

22. The method according to claim 19, wherein the selective histamine $H_3$ receptor agonist is R-(α)-methylbistamine, imetit, immepip, SKF 91606 or Sch 50971.

23. The method according to claim 19, wherein the selective histamine $H_3$ receptor agonist is administered after the onset of myocardial ischemia and/or myocardial infarction.

24. The method according to claim 19, wherein the selective histamine $H_3$ receptor agonist does not act on the central nervous system.

25. The method according to claim 19, wherein the selective histamine $H_3$ receptor agonist does not cross the blood brain barrier.

26. The method according to claim 19, wherein the histamine $H_3$ receptor is on a cardiac sympathetic nerve ending.

27. The method according to claim 19, wherein the histamine $H_3$ receptor agonist inhibits norepinephrine release from cardiac sympathetic nerve endings.

28. The method according to claim 19, wherein the histamine $H_3$ receptor agonist modulates the concentration of intracellular sodium.

29. The method according to claim 19, wherein the histamine $H_3$ receptor agonist is delivered in combination with at least one other agent in the treatment of cardiac dysfunction.

30. The method according to claim 19, wherein the other agent is one or more of the following: a β-blocker, a $Ca^{2+}$-channel blocker, an anti-arrhytbmic, an ACE inhibitor and an angiotensin receptor antagonist.

* * * * *

UNITED STATES PATENT AND TRADEMARK OFFICE
CERTIFICATE OF CORRECTION

PATENT NO.     : 6,884,809 B2
DATED          : May 13, 2005
INVENTOR(S)    : Levi et al.

It is certified that error appears in the above-identified patent and that said Letters Patent is hereby corrected as shown below:

Column 16,
Line 53, now reads "reducing cardiac dysfunctions ...", and should read
-- reducing cardiac dysfunction ... --.
Line 55, now reads "patholoaical excess of noreninephrine release, ...", and should read
-- pathological excess of norepinephrine release, ... --.
Line 56, now reads "comprising a administering...", and should read
-- comprising administering ... --.

Column 17,
Line 1, now reads "S-α-chloromethylhistarnine ..." and should read
-- S-α-chloromethylhistamine ... --.
Line 20, now reads "The method according to claim 1,...", should read
-- The method according to claim 10, ... --.
Line 23, now reads "agonist inhibits the $Na^+ H^+$...", and should read
-- agonist inhibits the $Na^+/H^+$... --.
Line 25, now reads "agonist inhibits the $Na^+ H^+$ exchanger...", and should read
-- agonist inhibits the $Na^+/H^+$ exchanger... --.
Line 36, now reads "N-type Ca2+ channel.", and should read -- N-type $Ca^{2+}$ channel. --.

Column 18,
Line 1, now reads "inhibiting the $Na^+ H^+$ exchanger...", and should read
-- inhibiting the $Na^+/H^+$ exchanger... --.
Line 4, now reads "histamine $H^3$ receptor agonist.", and should read
-- histamine $H_3$ receptor agonist. --.

UNITED STATES PATENT AND TRADEMARK OFFICE
CERTIFICATE OF CORRECTION

PATENT NO. : 6,884,809 B2
DATED : May 13, 2005
INVENTOR(S) : Levi et al.

It is certified that error appears in the above-identified patent and that said Letters Patent is hereby corrected as shown below:

<u>Column 18, (cont'd),</u>
Line 13, now reads "methylbistamine,...", and should read
-- methylhistamine, ... --.
Line 41, now reads "an anti-arrhytbmic,...", and should read
-- an anti-arrhythmic, ... --.

Signed and Sealed this

Sixteenth Day of August, 2005

JON W. DUDAS
*Director of the United States Patent and Trademark Office*